(12) United States Patent
Biancalana et al.

(10) Patent No.: US 12,253,355 B2
(45) Date of Patent: Mar. 18, 2025

(54) SYSTEM FOR TRACKING AN OBJECT

(71) Applicant: UNIVERSITA' DEGLI STUDI DI SIENA, Siena (IT)

(72) Inventors: Valerio Biancalana, Asciano (IT); Piero Chessa, Pisa (IT); Roberto Cecchi, Siena (IT); Marco Mandala', Poggibonsi (IT); Domenico Prattichizzo, Siena (IT)

(73) Assignee: UNIVERSITÀ DEGLI STUDI DI SIENA, Siena (IT)

( * ) Notice: Subject to any disclaimer, the term of this patent is extended or adjusted under 35 U.S.C. 154(b) by 100 days.

(21) Appl. No.: 18/017,390

(22) PCT Filed: Jul. 22, 2021

(86) PCT No.: PCT/IB2021/056657
§ 371 (c)(1),
(2) Date: Jan. 20, 2023

(87) PCT Pub. No.: WO2022/018691
PCT Pub. Date: Jan. 27, 2022

(65) Prior Publication Data
US 2024/0027176 A1 Jan. 25, 2024

(30) Foreign Application Priority Data
Jul. 22, 2020 (IT) .................. 102020000017776

(51) Int. Cl.
*G01B 7/02* (2006.01)
*G01B 7/004* (2006.01)
(Continued)

(52) U.S. Cl.
CPC ............. *G01B 7/023* (2013.01); *G01B 7/004* (2013.01); *G01R 33/0094* (2013.01)

(58) Field of Classification Search
CPC .......... G01B 7/02; G01B 7/023; G01B 7/004; G01B 7/14; G01R 33/00; G01R 33/02;
(Continued)

(56) References Cited

U.S. PATENT DOCUMENTS 6,129,668 A 10/2000 Haynor et al.
6,263,230 B1 * 7/2001 Haynor .................. A61B 34/20
600/424
(Continued)

FOREIGN PATENT DOCUMENTS

EP      2 884 372 A1    6/2015
WO      2010/091269 A1  8/2010

OTHER PUBLICATIONS

Xueliang Huo, et al., "A Magneto-Inductive Sensor Based Wireless Tongue-Computer Interface," IEEE Transactions on Neural Systems and Rehabilitation Engineering, vol. 16, Issue 5, pp. 497-504 (Oct. 2008).

*Primary Examiner* — Neel D Shah
(74) *Attorney, Agent, or Firm* — Maschoff Brennan

(57) ABSTRACT

A system (50) for tracking an object (1) comprises a magnetic field source (10) configured to be fixed to this object (1); a magnetometric data collection unit (20) that uses magnetic field sensors (22) fixed at predetermined positions on a support (23) to form an array (21), and that includes a sensor control unit (25) for controlling the magnetic field sensors (22); a data processing unit (30) configured to receive the magnetic field data from the sensor control unit (25) and to calculate from these data position coordinates of the magnetic field source (10) with respect to the array (21) forming a vector of such position coordinates which minimizes the distance between magnetic field values expected at the sensor positions (22) and magnetic field values collected by the collection unit (20), wherein the magnetic field source (10) is arranged to generate a local magnetic (Continued)

field (4), at the magnetic field sensors (22), of intensity set between 5 and 500 microtesla, so that the magnetic field sensors (22) detect both the local magnetic field (4) and the geomagnetic field (5), and wherein the data processing unit (30) is configured to recognize contributes of the local magnetic field (4) and of the geomagnetic field (5) in the magnetic field data, and is configured to determine location and of orientation coordinates of the magnetic field source (10) with respect to the array (21), as well as orientation coordinates of the array (21) with respect to the geomagnetic field (5). This way, an accurate tracking can be obtained of the displacements of the object (1) even if the array (21) is connected to a support that is movable with respect to an absolute reference system integral to the geomagnetic by fixing array to the subject's head.

25 Claims, 13 Drawing Sheets

(51) Int. Cl.
*G01B 7/14* (2006.01)
*G01R 33/00* (2006.01)
*G01R 33/02* (2006.01)
*G01R 35/00* (2006.01)

(58) Field of Classification Search
CPC ...... G01R 33/035; G01R 33/10; G01R 33/32; G01R 35/00
See application file for complete search history.

(56) References Cited

U.S. PATENT DOCUMENTS

| | | | |
|---|---|---|---|
| 9,911,358 B2* | 3/2018 | Ghovanloo | G09B 5/06 |
| 10,436,567 B2 | 10/2019 | Hautson | |
| 10,635,172 B1 | 4/2020 | Keller et al. | |
| 2007/0167703 A1* | 7/2007 | Sherman | A61B 5/06 600/407 |
| 2012/0281181 A1 | 11/2012 | Chen et al. | |
| 2014/0187907 A1 | 7/2014 | Duan et al. | |
| 2016/0299606 A1 | 10/2016 | Go | |
| 2017/0079551 A1 | 3/2017 | Henkel et al. | |

* cited by examiner

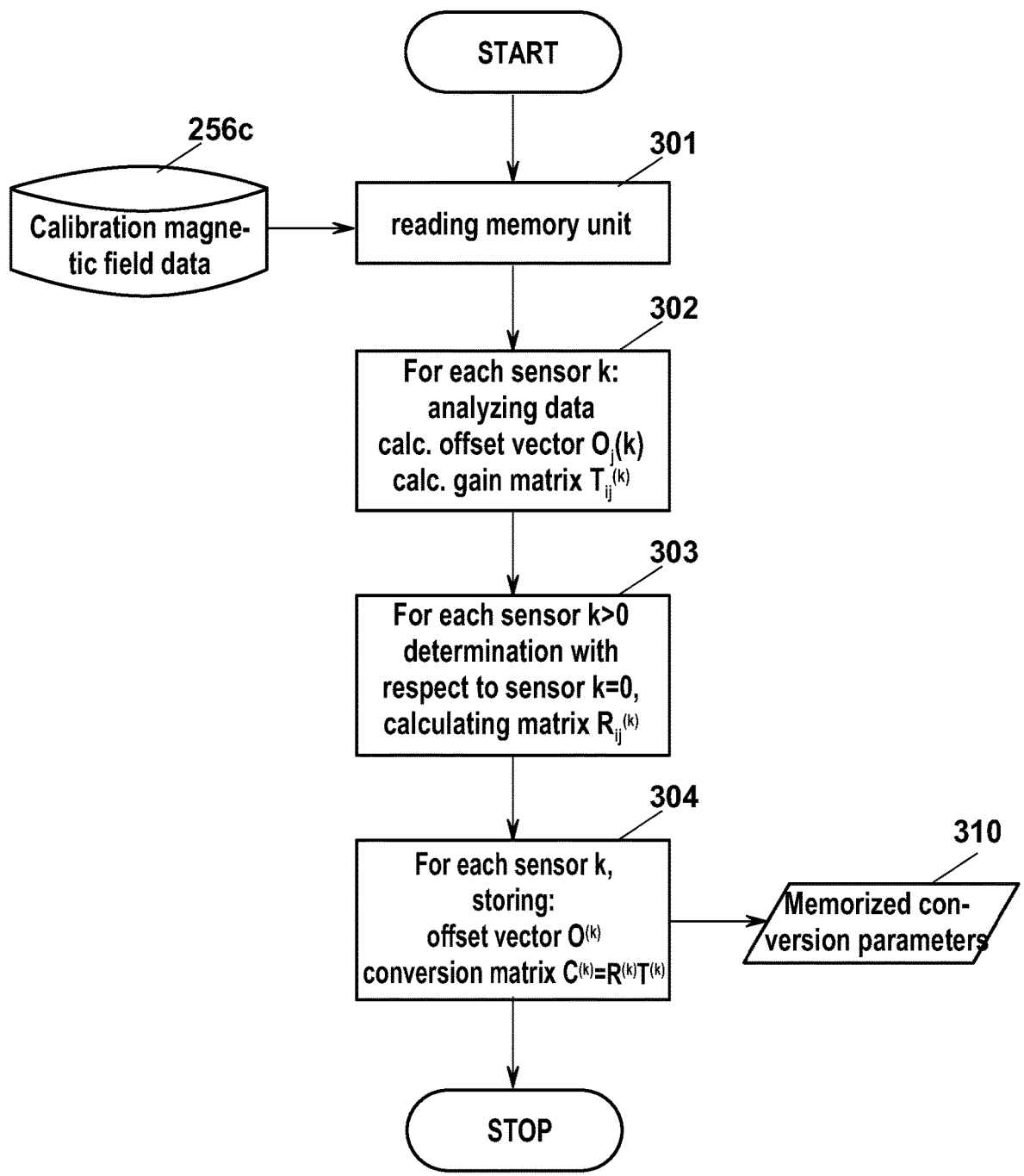

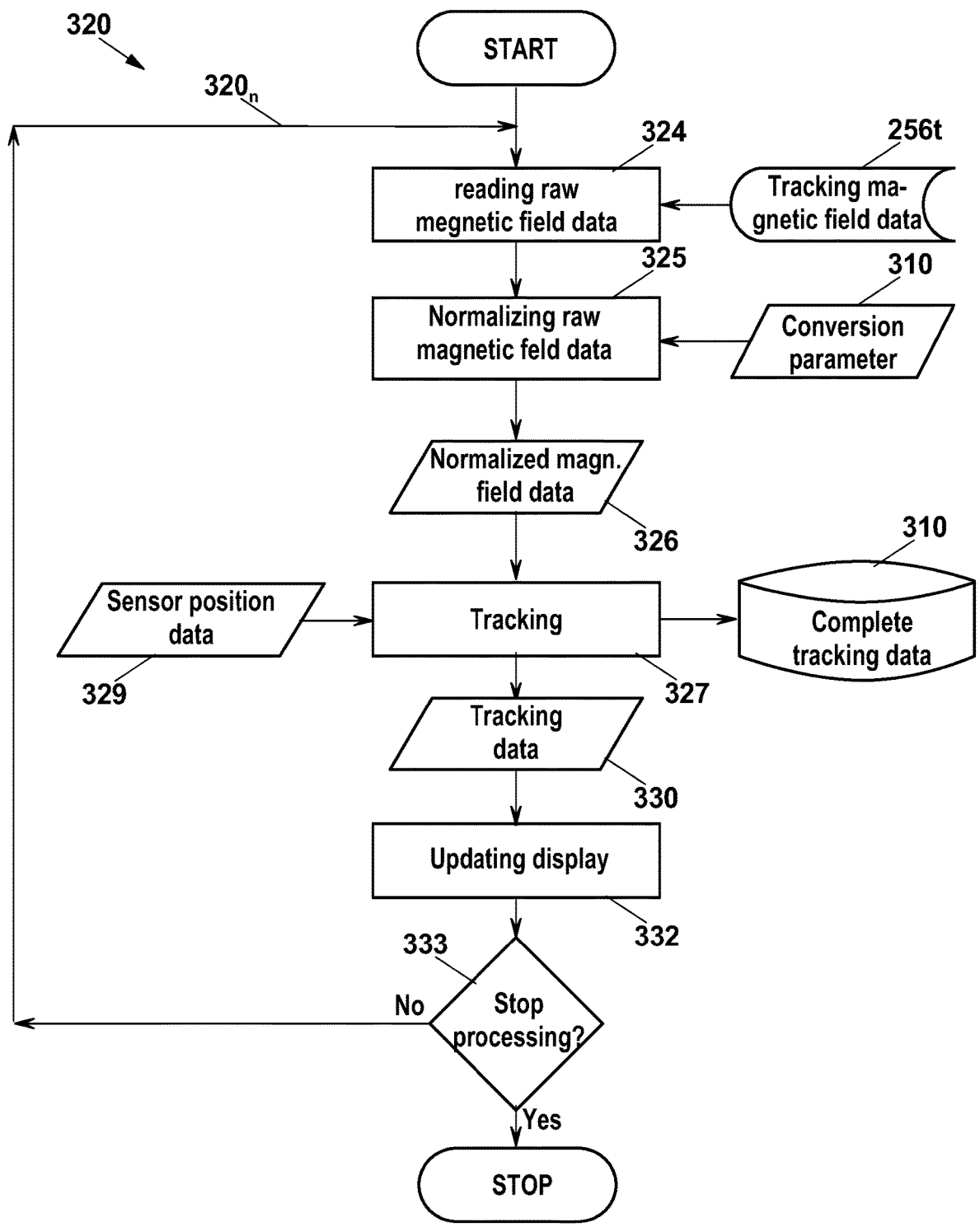

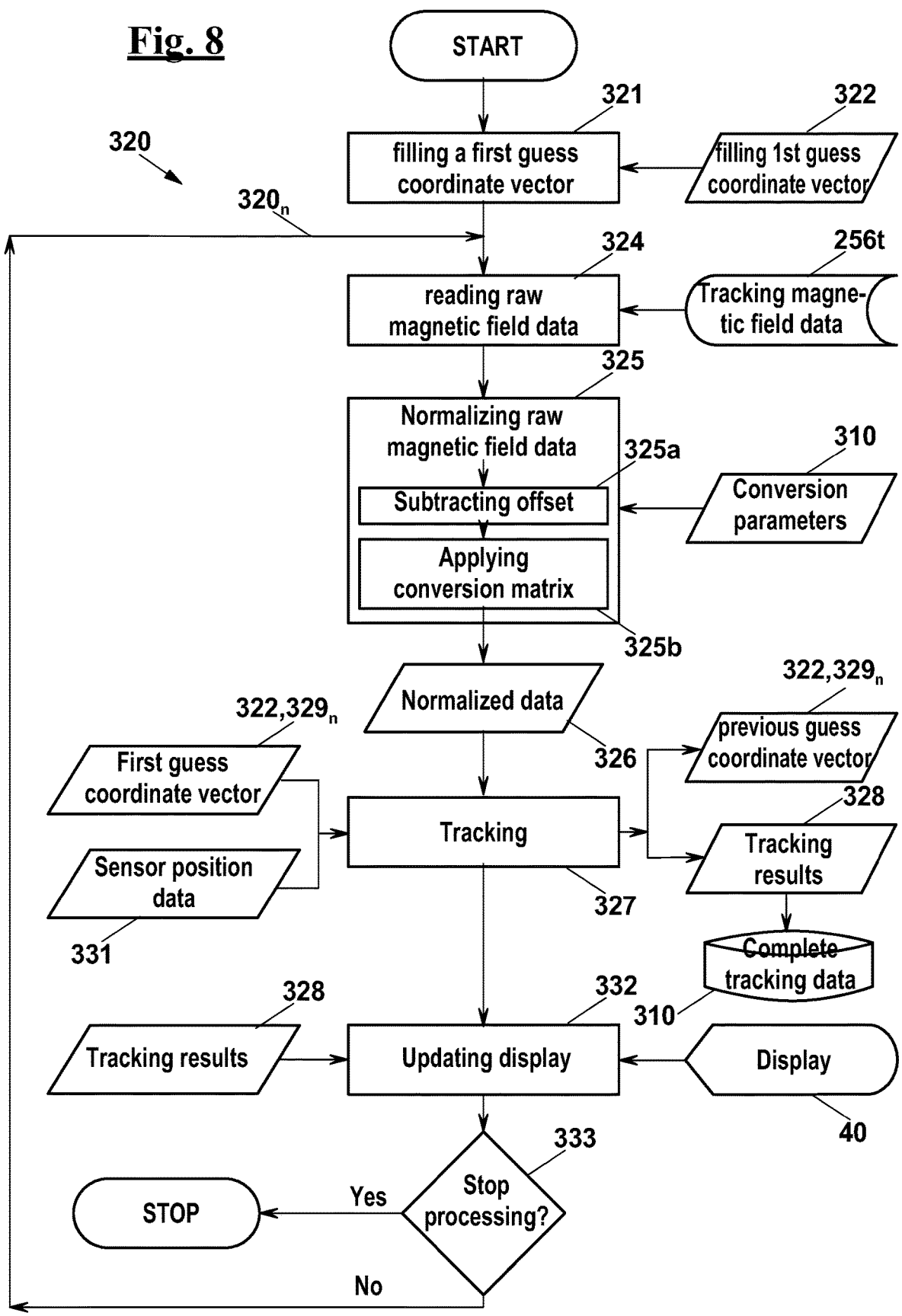

SYSTEM FOR TRACKING AN OBJECT

FIELD OF THE INVENTION

The present invention relates to a system, including magnetic field sensors, for performing the magnetic tracking of an object.

In other words, the system is suitable for following how changes the position of a movable object with time, i.e. for following the location and/or orientation object in the space, by measuring by said sensors the magnetic field generated by a magnetic field source integral to the object.

Moreover, the invention relates to some applications of this system, in particular to the tracking of the inclination and of the movements of the head and the eyes in order to interface seriously hindered patients with communication or robotic devices, or also for diagnostic purposes in neurologic patients. The tracking of the inclination and of the movements of the head and of the eyes can be useful also to check some machine operators, for safety or research purposes. Other applications are possible in such fields as:
   virtual reality (VR) and/or augmented reality (AR) technology;
   advanced graphic interfaces;
   handwriting storing and recognition;
   control of robotic surgical instruments,
and, more in general, to the real time or delayed tracking of the movement of objects having a negligible magnetic interaction.

PRIOR ART—TECHNICAL PROBLEMS

Systems are known for tracking magnetic field sources using magnetic field sensors. For instance, WO 2010/091269 A1 describes a system, useful in surgery or therapeutic applications, for detecting the position of a magnetic dipole, in which two detectors are provided at a distance from each other, and mutually arranged according to a known geometry. Each detector comprises at least three sensors, in particular magnetoresistive sensors, for measuring the magnetic field generated by the dipole. A data processing unit of the system is configured to receive measurement signals from the sensors and to calculate the position of the dipole starting from these signals.

U.S. Pat. No. 6,129,668 describes a system that can be used for detecting the position of a magnetic dipole coupled to a medical device within a patient's body. The position of the dipole is detected by measuring the intensity of the magnetic field generated by the magnet, using magnetic field sensors such as magnetoresistive magnetic sensors, which are arranged in known way, and by an iterative calculation procedure performed by a processor. In this procedure, an initial estimate of the dipole position-location and orientation-, a comparison of the intensity values of the magnetic field components expected according to the estimated position with the measured intensity values, a new estimate of the magnet position according to the difference between the expected values and the measured values, the computing of new expected values, and so on, until the expected values and the measured values substantially coincide. The estimated magnet position, with respect to a support, corresponds then to actual position, within a certain tolerance, and is displayed on a two-dimensional display. The document does not specify either the number of sensors, or the algorithm used, so that it cannot provide a skilled person indication to implement the above-described iterative procedure.

Also the process described in WANG et al., A Localization Method Using 3-axis Magnetoresistive Sensors for Tracking of Capsule Endoscope, Proceedings of the 28th IEEE EMBS Annual International Conference New York City, USA, Aug. 30-Sep. 3, 2006, uses an optimization method, according to Levenberg-Marquardt, for estimating five dipole position coordinates. This process is based on the progressive reduction of average quadratic distance, or of another distance, between values estimated values and measured values of the intensity of the magnetic field generated by a dipole.

EP 2 884 372 A1 describes a method and a device for localizing a plurality of magnetic objects by a network of magnetometres, in which an equation system is solved, said equation system conceived to be dynamically adapted to the number of magnetic objects to be localized.

In any case, the prior art systems can at most perform the tracking of an object with respect to a reference system integral to the sensors, i.e., integral to a support on which the sensors are fixed, but not with respect to a motionless reference system, if the sensors move during the measure.

This need is particularly felt in the case of the tracking of such movable portions of a subject's head as the eyeballs or the tongue. In some applications, these movements are used for operating robotic and/or communication apparatuses, and the support on which the sensors are fixed can be preferably worn on the subject's head. A similar need is felt field for virtual and/or increased reality applications.

For such applications, a high sampling speed is also required, which is not easily attained by the prior art tracking devices.

SUMMARY OF THE INVENTION

It is therefore a feature of the present invention to provide a system for tracking location and orientation displacements in in the space of an object having a magnetic field source, through a plurality of magnetic field sensors, which allows to refer such these displacements to a fixed reference system, i.e. to a reference system that is independent from the movement of the sensors.

It is also a feature of the present invention to provide such a system that allows a sampling speed higher than the speed allowed by the cited prior art systems, in particular a system that allows a sampling speed in the order of hundreds of samples per second, without reducing for precision, in order to track quickly evolving events, such as the movements of a subject's eyeballs.

It is also a feature of the invention to provide such a system that is easy and cheap to be manufactured.

These and other objects are achieved by a system for tracking displacements of in location and orientation in the space of an object having a magnetic field source, as defined by claim 1. Advantageous exemplary embodiments of the system are defined by the dependent claims, in particular specific objects are achieved by the apparatuses according to claims 12 to 20, said apparatuses based on tracking methods performed by the system according to the invention.

According to the invention, a system for tracking an object, i.e. a system for tracking location and/or orientation displacements in the space of the object, comprises:
   a data collection unit comprising:
      an array of magnetic field sensors fixed at respective predetermined sensor positions on a support and configured to measure magnetic field data, otherwise indicated as raw magnetic field data, said support configured to be arranged proximate to the object to be tracked;

a sensor control unit for controlling the magnetic field sensors, a connection means connecting the magnetic field sensors and the magnetic field sensors control unit, said connection means arranged to transfer the magnetic field data measured by the magnetic field sensors to the data processing unit, a magnetic field source comprising at least one magnetic dipole having a magnetic moment and configured to generate a local magnetic field and to be fixed to the object, wherein the magnetic field source is arranged to generate the local magnetic field, at the magnetic field sensors, with an intensity set between 5 and 500 microtesla, such that the magnetic field sensors detect, besides the local magnetic field, also the geomagnetic field;

a data processing unit configured to
  receive the measured magnetic field data from the sensor control unit;
  recover position data of said magnetic field sensors;
  fill a vector of
    location and orientation coordinates of the at least one magnetic dipole, i.e., of the magnetic field source, with respect to the array of the magnetic field sensors; and of
    orientation coordinates of the geomagnetic field, with respect to the array of the magnetic field sensors
  with first guess values;
  calculate, starting from the first guess values of the location and orientation coordinates of the at least one magnetic dipole, expected values of the local magnetic field at the positions of the magnetic field sensors, as the magnetic field generated by at least one magnetic dipole in a known position with respect to the magnetic dipole, for example, by the well-known literature equations providing the magnetic induction vector produced by a dipole at a known position with respect to it;
  calculate, starting from the first guess values of the orientation coordinates of the geomagnetic field, expected values of the geomagnetic field at the positions of the magnetic field sensors;
  calculate expected overall magnetic field values at the sensor positions as a resultant of the contribution of a magnetic induction vector of the local magnetic field generated by the magnetic field source and of a magnetic induction vector of the geomagnetic field;
  determine, starting from the magnetic field data, a vector of position coordinates comprising:
    location coordinates of the magnetic field source with respect to the array of the magnetic field sensors;
    orientation coordinates of the magnetic field source with respect to the array of the magnetic field sensors;
    orientation coordinates of the array of the magnetic field sensors with respect to the geomagnetic field, said vector minimizing a distance between:
    said expected overall magnetic field values at the sensor positions, and
    the measured magnetic field values obtained from the magnetic field data, wherein the data processing unit is configured to recognize in said magnetic field data contributes of the local magnetic field, determined starting from the location and orientation coordinates of the magnetic field source and of the geomagnetic field, determined starting from the orientation coordinates of the array of sensors, in order to:
  determine the location of the source in the space and the orientation thereof and, therefore
  obtain the mutual orientation of the source and of the magnetic induction vector of the geomagnetic field.

With such a choice of the magnetic field source, the local magnetic field has an intensity that is normally comparable with the intensity of the geomagnetic field, more in detail, the local magnetic field and the geomagnetic field have always the same order of magnitude or contiguous orders of magnitude. In fact, as well known, the geomagnetic field has an intensity that depends on the place on the Earth's surface between 25 and 65 microtesla. In other words, the local magnetic field is neither negligible nor excessively high with respect to the geomagnetic field, and vice-versa. For this reason, both magnetic fields are well estimated in the optimization process in use here.

This makes it possible, when computing the position coordinates of the magnetic field source, to precisely discriminate the respective contributes of the local magnetic field from the ones of the geomagnetic field and, accordingly, to determinate the orientation coordinates of the magnetic field source with respect to the geomagnetic field, regardless any displacement of the array of sensors, i.e. of the support on which the latter are fixed.

In the prior art, the geomagnetic field is normally neglected or treated as a source of noise that can lead to imprecisions while computing said coordinates. On the contrary, the method according to the present invention intrinsically include a precise detection of the mutual orientation of the geomagnetic field and of the sensors. Once precisely identified, the geomagnetic field, instead of providing a noise element in the tracking of the body, i.e. a source of imprecisions while computing the position parameters of the body, makes it possible to obtain more complete tracking data because the orientation of the measurement system is known with respect to it. In other words, accurate data about both the position parameters of the body and the direction the geomagnetic field, with respect to the sensors, increase the amount of data that can be obtained by the method, which makes it possible, in particular, to overcome the problems arising when the sensors are arranged on a mobile support.

As explained hereinafter, this is particularly advantageous for applications such as tracking the movements of a part of the body that can move with respect to another part of the body that is in turn movably articulated with respect to the body itself, to which the support with the array of sensors can be preferably mounted. This is the case, in particular of the movement of the eyeballs, the tongue, the jaw etc. with respect to the body, of the fingers with respect to the palm of a hand or of the fingers and/or the palm of the hand with respect to a forearm or arm, as well as of a foot with respect to a leg or of the foot and/or the leg with respect to a thig.

Moreover, even in those applications where it is not preferable or useful to arrange the support with the sensors on a movable body, by the system, it becomes unnecessary to costly shield the measurement environment, such as, for example a laboratory, from the geomagnetic field.

In another point of view, the method does not require very powerful magnets, which are usually too bulky for easily performing the tracking, or in any case it avoids important distortions due to the geomagnetic field, when the latter is not negligible with respect to the local magnetic field.

In particular, the magnetic field sensors are magnetoresistive sensors. Sensors of this type have been developed in the last decades to be used as components of solid-state compasses in largely widespread movable electronic devices, such as smartphones or the like. These sensors are well-suited for measuring magnetic fields intensity that are comparable with the geomagnetic field, as explained above. Such sensors also produce many general advantages, besides their low cost, high precision, possibility to provide already digitized data, minimum encumbrance, strength and minimum energy consumption. The low cost is a consequence of their continuously increasing use in portable consumer electronics.

In presently commercialized implementations, these devices allow sampling speeds of many tenths of samples per second, for instance 200 samples per second and more than three dynamic range decades, for example digitization at 14 bit, i.e. 16384 levels. The experiment has shown that this speed can be maintained also while processing data, provides processors are available having a processing speed of the same order of magnitude. This is particularly advantageous for tracking objects that quickly change position or direction such as a subject's eyeball.

As an alternative, the magnetic field sensors can be fluxgate sensors. In fact, also this type of sensors makes it possible to measure magnetic fields in an intensity range including the range of interest of 5-500 microtesla, moreover, they can be implemented at a relatively low cost and are modestly invasive.

The magnetic field source can be a magnetic field source that can be assimilated to a magnetic dipole mounted to the object, such as a magnet of size compatible with the size of the object to be tracked. In this case, the position coordinates, i.e. the tracking coordinates, are seven, and comprises:
- a first group for five dipole position coordinates with respect to the array of sensors, of which
  - three coordinates define the location, and
  - two angles define the orientation of the source, i.e., of a single dipole, with respect to the array of sensors, while dipole arrangements differing from one another by only a rotation about the dipole axis cannot be distinguished by the magnetic field sensors;
- a second group of two coordinates, i.e., two angles defining the orientation the array of sensors with respect to the geomagnetic field.

As an alternative, the magnetic field source can comprise a plurality of elements comparable to magnetic dipoles that have a predetermined orientation with respect to the object and that are rigidly connected to each other. In this case, the number of position coordinates increases to 8, since 3 angles independent from each other are required to define the position of the source, i.e., of the two mutually constrained dipoles, with respect to the array of sensors.

In order to obtain these coordinates, the number of the scalar sensors of the sensor array must not be lower than the number of tracking coordinates, i.e., than seven, if the magnetic field source can be assimilated to a dipole, and than eight if the magnetic field source can be assimilated to a plurality of dipoles rigidly connected to one another. In effects, various types of magnetic field sensors are commonly available in the form of vector sensors i.e., sensors having a plurality of axes, configured to measure two or three components of the magnetic induction vector. Therefore, in the case of triaxial vector sensors, number of such sensors must be larger than two.

Preferably, however, the array of sensors comprises at least a number of sensors high enough to provide a redundance level so high that the tracking process is at the same time steady enough to be not appreciably affected by noise and calibration imprecisions, and quick enough to be used in such critical applications as eyeball or tongue tracking. In fact, a number of vector sensors exceeding the minimum number, calculated as discussed above, has the advantage that the optimization method in use converges more quickly and/or to a more precise solution, or that the space within which the local field source can move is increased, while the measurements remain adequate to ensure the tracking. A number of sensors higher than the indispensable minimum, distributed over a higher space, also allows more easily fulfil the requirement that at least one subset of them is at a useful distance from the source when the latter, while moving, attains different positions, as discussed hereinafter.

The vector of position coordinates minimizing the distance between the expected i.e. calculated magnetic field values, and the measured magnetic field values can be computed by one of the many available iterative minimizing methods, well-known to an expert of the field, for instance by a Levenberg-Marquardt procedure.

Advantageously, the data processing unit, in order to obtain the vector of position coordinates which minimizes said distance, is configured to:
- define increment values for: the location coordinates of the magnetic field source; the orientation coordinates of the magnetic field source; the coordinates of the geomagnetic field;
- perform a sequence of steps including the steps of:
  - calculating the expected values of the local magnetic field;
  - calculating the expected values of the geomagnetic field;
  - calculating the expected values of the overall magnetic field;
  - calculating said distance;
  - checking whether the distance is larger than a predetermined target distance;
  - if the distance is larger than the predetermined target distance, then
    - update the guess values of: the location coordinates of the magnetic field source; the orientation coordinates of the magnetic field source; the coordinates of the geomagnetic field by increasing each of the guess values by respective the increment values; and
  - repeating the sequence of steps;
  - if the distance is not larger than the predetermined target distance, then
    - returning the guess values as the tracking values of:
      - the location coordinates of the magnetic field source with respect to the array of the magnetic field sensors;
      - the orientation coordinates of the magnetic field source with respect to the array of the magnetic field sensors;
      - the orientation coordinates of the array of the magnetic field sensors with respect to the geomagnetic field.

By the method described above, the first guess values of the location and orientation coordinates of the magnetic dipole with respect to the array of the magnetic field sensors, and the coordinates of the geomagnetic field with respect to the array of the magnetic field sensors can be selected in a wide range defined by such coordinates, as the inventors have confirmed by the experiments. In particular, as the first guess values one can select the nominal intensity of the earth's magnetic field, as locally known, the nominal intensity of the dipole, which is a feature of the magnet in use as the magnetic field source, a distance of the dipole from the barycenter of the magnetic field sensors equal, for instance, to 50 times the dipole size and a random orientation of the three vectors in their definition range, i.e. the two angles of the spherical coordinates including a latitude set between 0 and 180° and a longitude between 0 and 360°. As guess values in the subsequent iterations, normally, the values resulting from the iteration immediately previous can be used, apart from the cases indicated hereinafter.

Preferably, the data processing unit is also configured to:
if the distance is larger than the predetermined target distance,
compare the distance with a value of the distance as calculated in a previous iteration of the sequence of steps;
if the distance is not shorter than a value of the distance as calculated in a previous iteration of the sequence of steps,
recover previous guess values from the previous iteration of the sequence of steps, and
update the previous guess values by increasing each of them by an amount selected between the corresponding opposite value of the absolute value of said increment value and the absolute value of said increment value;
if the distance is shorter than a value of the distance as calculated in a previous iteration of the sequence of steps,
update the guess values increasing each of them by an amount selected between the corresponding opposite value of the absolute value of said increment value and the absolute value of said increment value;
repeat the sequence of steps.

Preferably, the data processing unit is also configured to:
before checking whether the distance is larger than the predetermined target distance, checking whether an elapsed calculation time and/or a number of operations performed since when the measured magnetic field data have been received by the data processing unit exceed upper limit values of the calculation time and/or of the number of operations, respectively;
if none of the upper limit values is exceeded, checking whether the distance is larger than the predetermined target distance and then perform the steps of claim 2;
if at least one of the upper limit values is exceeded, repeat the step of filling a vector with different first guess values and then perform the steps as in claim 1 and in claim 2.

In an exemplary embodiment, the magnetic field source comprises a plurality of magnetic dipoles, in particular two magnetic dipoles, rigidly connected to one another and differently oriented. This way, the orientation of the object to be tracked can be completely determined with respect to the array of the sensors. In fact, if the magnetic field source can be assimilated to a single dipole, the system is not able to discriminate positions of the array of sensors that only differ from one another by a rotation of the dipole about its own axis. In this exemplary embodiment, the position coordinates comprise three location coordinates of the magnetic field source with respect to the array of sensors, three orientation components the magnetic field source with respect to the array of sensors, and at least two orientation components of the geomagnetic field with respect to the array of the magnetic field sensors.

By measuring the geomagnetic field only, the system is not able to discriminate positions of the array of the magnetic field sensors that differ from one other by a rotation of the array about the direction of the geomagnetic field, i.e. the system cannot detect rotations of the array of the sensors about the direction of the geomagnetic field. Therefore, such a system is not powerful enough to obtain data about the three angular coordinates describing the direction of the array. However, in order to fully characterize the rotational displacements of the array of the sensors, the system can provide the measurement of a different vectorial amount integral to environment and not parallel to the geomagnetic field, as in the exemplary embodiments described hereinafter.

The Iterative Methods Used

In an exemplary embodiment, the data collection unit comprises a gravimetric sensor. This way, it is possible to simultaneously measure the Earth's gravitational field besides the geomagnetic field. This makes it possible to completely determinate the direction the array with respect to an external reference system that is in turn referred to the directions of the geomagnetic field and of the gravitational field. In this exemplary embodiment, the coordinates comprise three location coordinates of the magnetic field source with respect to the array of sensors, at least two orientation components the magnetic field source with respect to the array of the magnetic field sensors and three orientation components of the array of the magnetic field sensors with respect to an external reference system that is in turn referred to the directions of the geomagnetic field and of the gravitational field.

In an alternative exemplary embodiment, the system comprises a magnetic field generator device, integral to the environment, configured to generate an auxiliary magnetic field variable with time in a known way and not parallel to the geomagnetic field. In this exemplary embodiment, the coordinates comprise three location coordinates of the magnetic field source with respect to the array of sensors, at least two orientation components of the magnetic field source with respect to the array of the magnetic field sensors and three orientation components of the array of the magnetic field sensors with respect to an external reference system that is in turn referred to the directions of the geomagnetic field and of the auxiliary magnetic field. In the data analysis both the static geomagnetic field and the variable auxiliary magnetic field are identified separately. By the measurement of these two independent vectorial amounts all three angular coordinates of the array can be determined. The direction the array of the sensors is then fully characterized by magnetic field measurements only.

Preferably, the auxiliary magnetic field is substantially homogeneous, i.e. it is independent from the measurement position. This reduces the required computing power for causing the process algorithm to converge to a solution, besides allowing a higher tolerance with respect to the displacements of the sensors.

Preferably, the connection means comprises a plurality of independent buses, each of which connects a respective magnetic field sensor with the sensor control unit. By The parallelizing this way the communication between the sensors and the control unit, it becomes possible to exploit at best the data collection speed capacity of the sensors and to perform simultaneous measurements to be used for the tracking. In these conditions, the inventors have realized that sampling speeds can be obtained up to 200 samples per second, which is widely compatible with the most exigent applications among the ones described hereinafter, such as tracking a subject's eyeball or advanced detection of graphometric features, or applications in the field of the virtual/increased reality. In particular, the independent connections can be advantageously implemented by using I²C buses as independent buses.

The experiment and the simulations have shown that the can be scaled in a wide range of sizes, apart from the technological constraints deriving from the minimum distance that must be present between the magnetic field sensors for correctly detecting their positions, and taking into account of the size of the integrated circuits that include the sensors and/or must be added/arranged on the support for driving the magnetic field sensors themselves. In particular, the better performances are achieved when the ratio between the linear dimension of the magnetic field sources, in particular the cubic root of the volume, and the linear dimension of the array of the sensors, in particular the average of the distance between the sensors, or of a subset thereof, and the magnet, is set between 1/30 and 1/100, in particular between 1/40 and 1/60. Preferably, the magnetic field source is selected in such a way that the ratio between a linear dimension of the array of the magnetic field sensors and of the magnetic field source is about 50. This way, the intensity of the local magnetic field, as detected at the sensors, and the intensity of the geomagnetic are comparable, i.e. they have the same order of magnitude or contiguous orders of magnitude. In particular, if during the tracking the magnetic field source is kept in a central portion of the space with respect to the sensors, all the sensors contribute with signals in which the contribution of the local magnetic field is not negligible.

Preferably, the magnetic field source comprises a magnetic material having a magnetic remanence larger than 800 k/Am, in particular it comprises a Neodymium magnet. This is particularly advantageous in those applications where the magnetic field source must be associated to a part of the body, as in the case of the eyeball tracking. In fact, such magnetic materials make it possible to use minimum-size magnets that are minimally invasive to said part of the body.

Advantageously, the data processing unit is configured to perform a calibration step comprising the steps of:
receiving calibration-intended magnetic field data, as measured by said magnetic field sensors and obtained from homogeneous magnetic field measurements carried out while changing the orientation in the space of the array of the magnetic field sensors;
computing conversion parameters for each magnetic field sensor starting from the calibration-intended magnetic field data.

In particular, said magnetic field sensors are triaxial magnetic field vector sensors and the compensation parameters comprise, for each magnetic field sensor, three offset values, three gain correction coefficients and three orthogonality defect compensation coefficients. In particular, one of the triaxial vector sensors defines the cartesian reference system of the array and for all the other sensors three coordinates are determined that define the orientation in that reference system. Briefly, 9 conversion parameters are defined for a reference sensor and 12 parameters for all the other sensors. The magnetic field sensors can however be sensors having one or two axes, provided that their number is correspondingly increased, with respect to the minimum calculated number thereof and to a preferably higher number, in order to ensure a suitable redundance, as mentioned above.

Advantageously, the data processing unit is configured to perform a step of calibrating said magnetic field sensors, the data collection unit comprises a temperature sensor, from which the magnetic field sensors control unit is configured to obtain an actual temperature of the magnetic field sensors, and to:
store a calibration temperature, at which the calibration is carried out, into a temperature memory unit;
upon receiving a processing start command signal, calculate the difference between the actual temperature and the calibration temperature;
if the difference is higher than a predetermined value, emit an alarm signal,
wherein a means is provided for notifying the alarm signal to a user. This way, the user has a criterium to start a new calibration cycle of the magnetic field sensors. This way, the system is less likely to be used in a calibration defect condition, which occurs because the more the use temperature, beyond a certain limit, differs from the calibration temperature, the more the calibration parameters determined at that calibration temperature are suitable.

In an exemplary embodiment, the magnetic field sensors control unit is integral to the support, whereas the data processing unit is an external data processing unit selectively connectable to the sensors control unit, and the data collection unit comprises, integral to the support, a non-volatile memory unit for such magnetic field data, preferably an EEPROM memory unit, and a housing for an internal battery for electrically supplying the magnetic field sensors control unit and the magnetic field sensors. This allows the data collection unit to operate independently from the external data processing unit, for example a personal computer or an equivalent device, and independently from a power supply network. This way, it is possible to orient the array of the magnetic field sensors in the space without significant constraints. This makes it easier to collect data required by the calibration procedure, which involves many homogeneous field measurements, typically geomagnetic field measurements, that are carried out arranging carried out the array of the magnetic field sensors in many angular positions. To this purpose, the support must be rotated freely along with the array of the magnetic field sensors: this step would be uncomfortable or even impossible to be carried out in the presence of electric supply and/or data input cables towards the data processing unit.

Advantageously, the data processing unit is configured to perform a step of calibrating the magnetic field sensors, and
the collection unit is arranged to be electrically supplied selectively by an internal battery or by an external power source,
the magnetic field sensors control unit comprises an automatic switch-off means for discontinuing an electric supply of the data collection unit from the internal battery upon receiving an end-of-calibration signal.
This makes it possible to limit the internal battery consumption and, substantially, to reduce the required internal battery capacity and size, as well as the weight and the encumbrance of the data collection unit. In fact, in some applications, as described hereinafter, the data collection unit is configured to be worn on a subject's head.

Preferably, the automatic switch-off means is configured to discontinue the electric supply of the data collection unit from the internal battery once a predetermined delay time has elapsed after receiving the end-of-calibration signal.

This makes it possible to connect the data collection unit to an external power source without turning off the data collection unit, in particular without removing the power supply to the magnetic field sensors. The external power source can be a power electric supply unit associated with an USB port of a personal computer that works as the data processing unit, the USB port configured to be connected to the USB port of the collection data unit. This is particularly advantageous if magnetoresistive magnetic field sensors are used. In fact, these sensors normally include a reset means for that is automatically activate whenever the sensor is switched on. This event could cause uncontrollable change of the offset and of the gain of the many sensors, which would make the calibration step result useless.

In another exemplary embodiment, also the data processing unit is integral to the support. This way, it is possible to obtain an apparatus for size compact and preferably used regardless of the presence of a computer outer as a personal computer.

According to an aspect of the invention, an apparatus for controlling a peripheral device according to the movements of a movable portion of the head of a subject, in particular of a patient with reduced mobility, comprises the above-described tracking system, wherein the support is configured to be fixedly worn on the subject's head of the subject and the magnetic field source is configured to be fixed to the movable portion of the subject's head, wherein the apparatus comprises an interface and control unit for controlling a peripheral device, the interface and control unit configured to receive the position coordinates of the magnetic field source from the tracking system, and to perform a generation of control signals for the peripheral device starting from said coordinates.

In particular, the movable portion of the head can be the tongue, or an eyeball, or a jaw, or an eyelid or an eyebrow.

In an exemplary embodiment, the apparatus is an apparatus for controlling a peripheral device according to the movements of a subject's tongue, including the above-described tracking system, where the magnetic field source is configured to be applied to the patient's tongue.

Such an apparatus can be advantageously used by a patient who cannot use his/her limbs or whose limbs are severely impaired, in order to control robotic and/or communication apparatuses through a computer. In fact, patients who suffer from serious neurologic impairing diseases, have often a residual capacity to control tongue movements.

Such an apparatus can also be used for controlling robotic and/or communication devices by a healthy user who is using his/her limbs in a different activity.

Advantageously, the apparatus comprises a sound detector connected to the interface and control unit, and the interface and control unit comprises a means for recognizing a subject's verbal communication act, and is configured to discontinue the generation of control signals upon recognizing the verbal communication act. This way, the subject is enabled to talk without any effect of the corresponding tongue movement on the controlled peripheral device.

In an exemplary embodiment, the apparatus is an apparatus for controlling a peripheral device according to the movements of a subject's eyeball, said apparatus including the above-described tracking system, where the magnetic field source is configured to be applied to the patient's eyeball.

Advantageously, the magnetic field source is a magnet configured to be integrally connected to a contact lens wearable by the subject. The apparatus can also comprise the contact lens with the magnet inserted therein. Preferably, the magnet has a transversal dimension, such as a diameter, shorter than 3 mm and a thickness shorter than 1 mm, more preferably a transversal dimension shorter than 2 mm and a thickness shorter than 0.5 mm.

Such an apparatus can be advantageously used as a diagnostic apparatus to characterize physiologic or pathologic aspects of the ocular movements, which can also be related to a condition of the vestibular apparatus, or in some tests in which a patient is requested to fixedly look at an object while rotating his/her head. In fact, the apparatus can follow at the same time the movement of the eye with respect to the sensors, integral to the head, and the movement of the sensors with respect to the geomagnetic field. The simultaneous tracking of the magnetic field source and of the array of sensors allows correlating imposed or spontaneous movements of the head with the eye movements, and it is therefore useful for such diagnostic applications.

Such an apparatus can be advantageously used by a patient who cannot use his/her limbs or whose limbs are severely impaired, in order to control robotic and/or communication apparatuses through a computer working as an interface. In fact, patients who suffer from serious neurologic impairing diseases, have often a residual capacity to control eyeballs movements. For the above-mentioned applications, for example, it is possible to use the gaze direction of a patient looking at a panel displaying icons corresponding to specific commands for peripheral device to that patient.

With respect to some corresponding prior art apparatuses, which use such devices as infrared video cameras to follow the movements of the eyeballs, the apparatus according to the invention has a definitely lower cost and smaller size. At the same time, the apparatus according to the invention is much stronger, i.e. more reliable. In particular, this apparatus can perform an accurate tracking when of circumstances are present that are partially unknown or that are not considered, such as involuntary eyelid movements, which discontinue the tracking of the movements, the presence of a infrared light reflecting pigment misleading the video camera and other conditions, for example in case of particularly bright and/or light eyes.

The apparatus according to the present exemplary embodiment also overcomes the problems of ocular tracking devices in which search coils are used. In fact, in the invention, no cabled electric connections are required between the contact lens, i.e. between the search coil incorporated therein, and the logical unit or magnetic field sensor control unit that collects the measured data. Therefore, the invention is advantageously less invasive.

Such an apparatus can also be used for an objectively check whether a subject is too tired to be engaged in a critical activity such as driving a means of transport, as in case of professional aircraft pilots. Even in this case, the simultaneous tracking of the magnetic field source and of the array of sensors makes it possible to correlate the head movements with the eyeball movements and, accordingly, to recognize typical movement combinations of wearying conditions that cannot be accepted when for performing such activities.

The apparatus can also be used for investigating a subject's sleep evolution and features, the sleep notoriously including two stages, i.e. the REM (Rapid Eye Movements) sleep, characterized by quick movements of the eyeballs, and the NREM (non-REM) sleep.

The apparatus can also be advantageously used in the field of the virtual reality, still as a gaze direction detection instrument, also in this case thanks to the possibility of tracking the eyeball with respect to the head and the head with respect to the geomagnetic field, i.e., to a motionless reference system, with the above-mentioned cost and size advantages.

According to another aspect of the invention, a three-dimensional pointing apparatus, in particular a three-dimensional writing device comprises:
- a fixed three-dimensional drawing pad, i.e. a drawing box, which performs in 3D all the functions commonly performed in 2D by a drawing pad, said three-dimensional drawing pad reproducing a drawing environment or command environment;
- a pointing device comprising a portion, in particular a tip portion, that is configured to be displaced in the three-dimensional drawing pad;
- a display unit configured to perform a representation of graphic elements;
- a data processing unit configured to order the display unit to perform the representation of the graphic elements responsive to the position and/or to an active/inactive status of the pointing device in the drawing pad;
- the above-described tracking system, wherein the magnetic field source is arranged at said portion of the pointing device, where the pointing device is the object to be tracked, and wherein the support is integral to the three-dimensional drawing pad.

In an exemplary embodiment, the pointing apparatus can also comprise a shield element of a ferromagnetic material arranged for moving with respect to the magnetic field source, in order to shield the magnetic field source at a variable shield degree with respect to the sensors, so that the tracking system, through the sensors, can detect intensity changes of the local magnetic field, and wherein the data processing unit is configured to modify a display parameter of one of the graphic elements, in the display unit, according to the shield degree of the magnetic field source with respect to the sensors. This way, in case of objects moving in a small space, in which, without an adjustable shielding, the module of the magnetic induction vector detected by the sensors is substantially the same even if the direction of the magnetic source detected by the system changes, the intensity of the magnetic field source is also exploited to represent some features of the graphic objects.

In particular, the display parameter can be a line thickness, a line or picture color or color tonality, a line or picture hatch density.

According to another aspect of the invention, an apparatus for measuring a subject's graphometric features comprises:
- a pen-like element which can be operated configured to be operated by a hand of the subject;
- a sensitive surface configured to feel the contact of a tip of the pen-like element;
- a computing means associated with the sensitive surface and configured to associate a plurality of graphometric features to a writing contact of the pen-like element on the surface,
- the above-described tracking system, wherein the magnetic field source is arranged at a portion of the pen-like element, in particular at an end of the pen-like element opposite to the tip of the pen-like element, wherein the pen-like element is the object to be tracked, and wherein the support is integral to the sensitive surface,
wherein the graphometric features comprise parameters associated with orientation parameters of the magnetic field source. In particular, the graphometric features comprise two inclination angles of the pen-like element during the writing contact.

Such an apparatus makes it possible to determine data that cannot be obtained by the handwriting as such, and also allows determining data that cannot be obtained even using the most advanced graphometric apparatuses, as those that are able to detect the pressure a subject exerts on a writing support with the pen-like element. In particular, the apparatus according to the invention makes it possible to recognize, besides the purely graphic features or the writing pressure, also such data as the orientation the subject imposes to the pen-like element or to the pen while writing.

Such an apparatus can be advantageously used in applications for checking the authenticity of a subject's signature, since it makes it possible to determine a larger number of postural parameters of a subject when he/she writes his/her own signature than in the currently known recognition systems and, accordingly, it allows using such parameters for confirming the authenticity. In fact, a person who is able to forge signatures by copying them from a normal two-dimensional representation, even if this representation is available, would have data to repeat also the inclination of the pen or pen-like element. Moreover, the apparatus is advantageously used for investigating implications physiologic, and even pathologic aspects of some features of a subject's handwriting.

According to another aspect of the invention, an apparatus for tracking displacements of a surgical tool in a patient's body comprises the system according to the previous description, wherein the magnetic field source is arranged at a portion of the surgical tool, in particular at an end portion of the surgical tool.

In particular, before introducing the surgical tool into the patient's body, a ferromagnetic tracer can be injected into a predetermined region of the patient's body. This makes it possible to precisely measure the distance between the magnetic field source, which is arranged at the end of the surgical tool, and the injected magnetic tracer.

This way, it is possible to perform an anatomical and surgical identification of a sentinel lymph node in an oncologic disease, or the surgical identification of hardly detectable anatomical structures at a submillimeter resolution, without using radioactive tracers and radiologic techniques providing ionizing radiations.

According to another aspect of the invention, an apparatus for tracking the displacements of the fingers of a of a subject's hand, comprises at least one tracking system as that above described, wherein:
- the magnetic field source is arranged at a portion of a respective finger of the hand, in particular at a phalanx;
- the support with the array of the magnetic field sensors is configured to be fixed to the wrist of the hand or to the corresponding forearm of the subject.

This way, it an apparatus is provided that is useful for virtual reality and augmented reality applications, and also has the advantages provided by the device according to the invention. With respect to of the prior art to track the movements of the fingers in virtual and/or augmented reality applications, the position of the fingers can be tracked with time regardless the unavoidable wrist and forearm movements, to which the array of sensors is integrally connected, in the same way as the tongue and of eyeball movements can be tracked by "neutralizing" the head movements, to which the sensors are integrally connected. With respect to the prior art, also in this case, it is possible to avoid the use of means for detecting the position and tracking the movement of the fingers, such as video cameras and the like, which are expensive, bulky, of difficult to install and less reliable in the presence of some environmental noises. Even the precision of the tracking is improved with respect to the prior art means.

Moreover, the fingers above identified can also be the fingers of an arm robotic.

BRIEF DESCRIPTION OF THE DRAWINGS

The invention will be now shown with the description of its exemplary embodiments, exemplifying but not limitative, with reference to the attached drawings, in which:

FIG. 6 is a flowsheet that shows the operations performed by the magnetic field data processing unit operating in "calibration" mode;

FIGS. 7 and 8 are flowsheets of the operations performed by the magnetic field data processing unit operating in "tracking" mode, in different exemplary embodiments of the invention;

FIGS. 10-16 diagrammatically show apparatuses based on the system according to the invention, and in particular, FIG. 10-10A, an apparatus for tracking a subject's tongue;

FIG. 11-11B, an apparatus for tracking at least one eyeball i.e. the gaze direction of a subject;

FIGS. 12 and 13, a three-dimensional pointing apparatus in two different exemplary embodiments;

FIG. 14, an apparatus for detecting graphometric features of a subject;

FIG. 15, an apparatus for tracking the fingers of a subject.

DETAILED DESCRIPTION OF THE INVENTION

Figure 1:
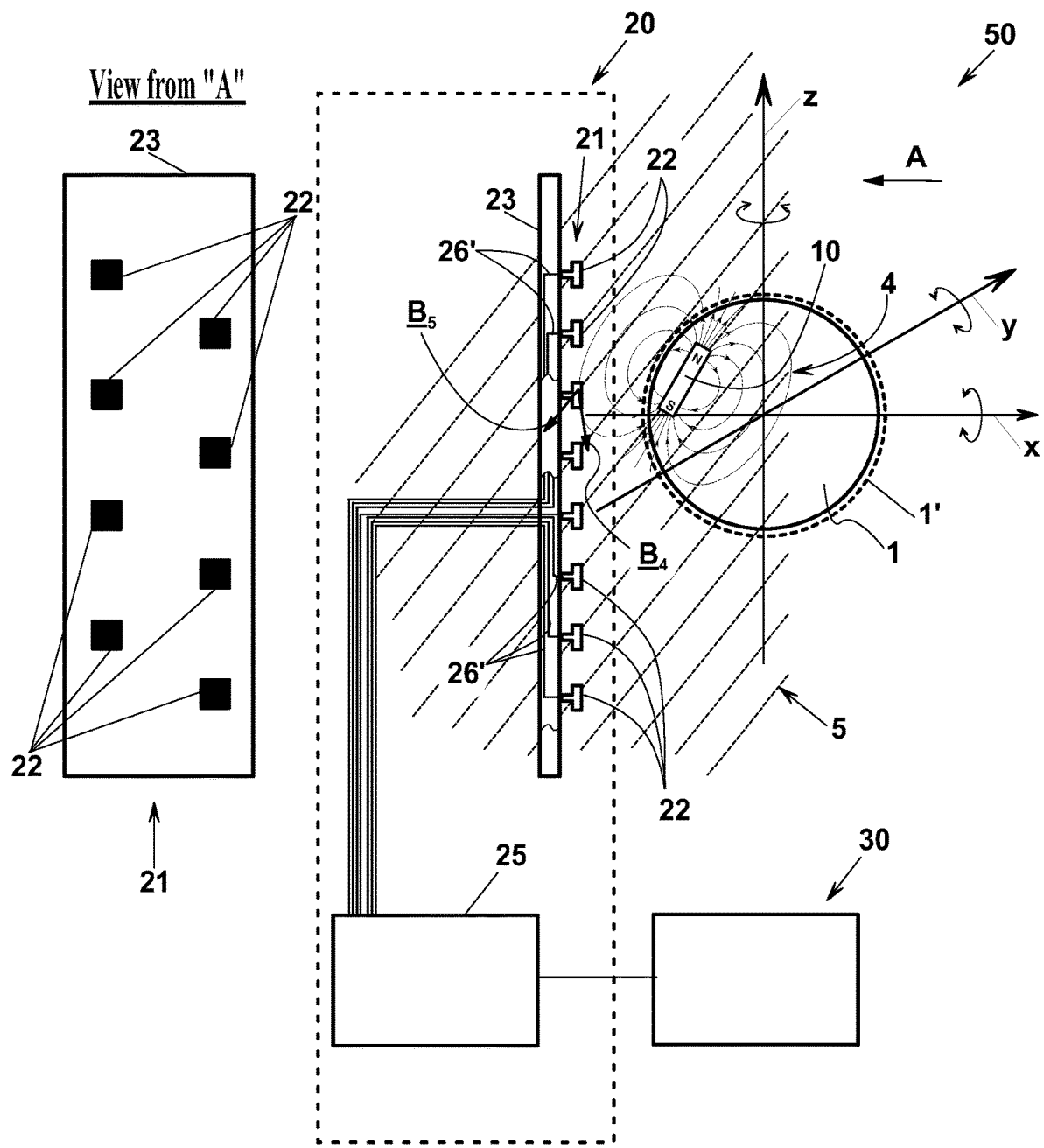
FIG. 1 diagrammatically shows a system according to the invention.

With reference to FIG. 1, a system 50 is described for tracking an object or a target 1, i.e. to follow the evolution with time of the position of object 1. System 50 essentially comprises three parts, i.e. a magnetic field source 10, a data collection unit 20 and a data processing unit 30.

Collection unit 20 comprises a support 23 on which magnetic field sensors 22 are fixed forming an array 21. Therefore, magnetic field sensors 22 have predetermined positions with respect to support 23, generally known apart from the normal mounting tolerances. Magnetic field sensors 22 are configured to detect a magnetic field at their own respective positions.

The magnetic field source can be schematized as a dipole 10 fixedly arranged on object 1, or as a plurality of dipoles, in particular two dipoles fixedly arranged on object 1, as described more in detail hereinafter. The position of object 1 is determined by identifying the position of dipole 10 by collection unit 20 and data processing unit 30. In a generic point and, in particular, at points where sensors 22 can be arranged, dipole 10 generates a local magnetic field 4 whose magnetic induction vector $B_4$ can be calculated in a known way by knowing the magnetic moment of the dipole and the position of the point with respect to dipole 10.

Normally, the magnetic field determined by sensors 22 include a contribution of earth's magnetic field or geomagnetic field 5, which can be considered substantially homogeneous, i.e. uniform at least in all the space occupied by array 21 where the measurements are made. The module of magnetic induction vector $B_5$ of this geomagnetic field has a value that is normally set between 25 and 65 microtesla and that depends on the place on the Earth's surface where it is detected. In the presence of the magnetic field source or dipole 10, the magnetic field also includes a contribution of local magnetic field 4 generated by dipole 10. Local magnetic field 4 is not homogeneous, i.e., it changes with the position at which it is measured with respect to dipole 10, in particular magnetic induction vector $B_4$ has a module depending on the inverse cube of the distance of the measurement point from dipole 10, and its direction is given by field lines that are known when the shape and the position of dipole 10 are known.

According to the invention, magnet 10 is selected in such a way that, at the positions of magnetic field sensors 22, the contribution $B_4$ of local magnetic field 4 generated by dipole 10 is comparable with the contribution $B_5$ of geomagnetic field 5, i.e., in such a way that the modules of the two contributions have the same order of magnitude, or have contiguous orders of magnitude. This is obtained by using a dipole 10 that, in the above-described position range, generates a magnetic field whose intensity, i.e. the module of magnetic induction vector $B_4$, is set between 5 and 500 microtesla.

In FIG. 1 an object to be tracked 1 is shown having a substantially spherical shape, rotatably arranged about three orthogonal axes x, y, z in a housing 1' that also has a spherical shape. However, this does not limit either the shape or the number of degrees of freedom, i.e. the possible movements of object 1.

For example, magnetic field source i.e. dipole 10 can be provided by a Neodymium Nd magnet, in particular a 1 Tesla or about 800 kA/m Nd magnet.

The inventors have discovered that, by the magnetization level provided by such a magnet, an intensity of 5-500 microtesla at the positions of magnetic field sensors 22 of array 21 can be obtained if magnetic field source 10 is selected in such a way that the ratio between a linear dimension of array 21 of sensors 22 and a linear dimension of magnetic field source 10 is set between 40 and 60, preferably if this ratio is about 50, in particular, for a subset of at least three of sensors 21, intended as triaxial vector sensors.

This provides a scale-up criterium for magnetic field source 10 and for data collection unit 20 of system 50 of the invention, apart from the obvious technological constraint due to the minimum distance that must be present between magnetic field sensors 22 to correctly detect their positions, and taking into account the dimensions of the integrated circuits, not shown, that include the sensors and/or must be added/arranged on support 23 in order to control the magnetic field sensors 22 themselves.

Magnetic field sensors 22 are preferably magnetoresistive sensors, even if different sensors can be used, for instance, fluxgate sensors. Preferably, magnetic field sensors 22 are vector sensors, i.e. each sensor unit is configured to provide three scalar values corresponding to the three components of magnetic induction vector B of the detected magnetic field.

Figure 2:
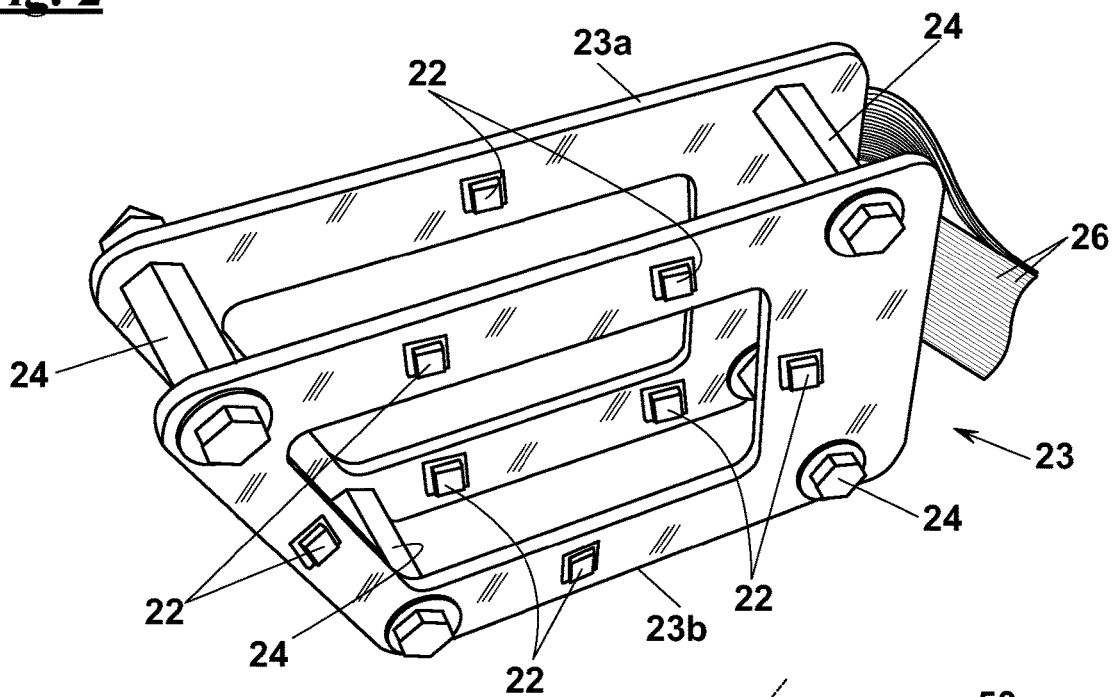
FIG. 2 is a perspective diagrammatical view of a support with an array of magnetic field sensors, according to an exemplary embodiment of the invention.

A possible exemplary embodiment of support 23 is shown In FIG. 2, which in the experiments has allowed particularly precise trackings. In this exemplary embodiment, support 23 comprises first and second support surfaces 23$a$ and 23$b$ parallel to each other, the sensors being distributed on both the support surfaces 23$a$ and 23$b$. In particular, as shown in FIG. 1, at least one magnetic field sensor 22 is fixed to second support surface 23$b$, the other sensors arranged on first support surface 23$a$. Even if support 23 shown in the drawings always comprises flat support surfaces 23, 23$a$, 23$b$, other shapes are also possible, provided magnetic field sensors 22 are fixed to support 23 in relative predetermined positions, not lying on a same plane.

Moreover, FIG. 2 relates to a particular case in which array 21 comprises seven vector sensors 22, even if the number of sensors can differ from the number which indicated here, which has the effects that will be described hereinafter. In this case, each magnetic field sensor 22 provides three scalar values that are the three components of magnetic induction vector B in a reference system integral to support 23.

Still with reference to FIG. 1, system 50 also comprises a sensor control unit for controlling magnetic field sensors 22 including a plurality of ports, not shown, for corresponding independent buses 26', for example I$^2$C buses, each of which connects a magnetic field sensor 22 with a respective port of sensor control unit 25, the set of the doors and of independent buses 26' constitutes a connection means 26 connecting magnetic field sensors 22 and sensor control unit 25. This way, sensor control unit 25 can receive at the same time magnetic field data measured in the field by all magnetic field sensors 22.

System 50 also comprises a data processing unit 30 configured to receive the raw magnetic field data from magnetic field sensor control unit 25. Sensor control unit 25 and data processing unit 30 are distinct logical units, implemented according to various architectures.

Figure 3:
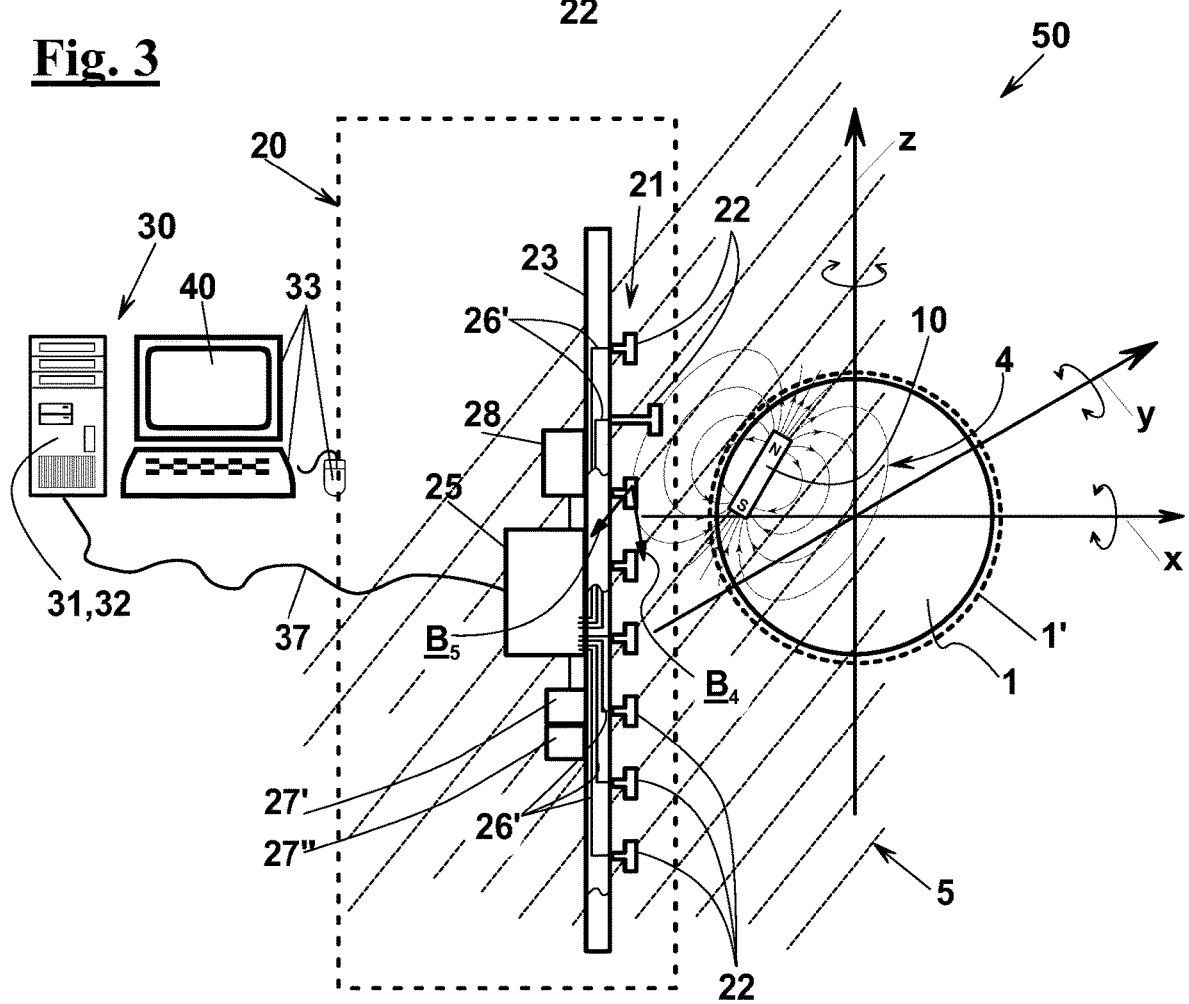
FIG. 3 diagrammatically shows a system according to an exemplary embodiment of the invention, in which the data processing unit is implemented with a calculation device remote with respect to the data collection unit, for example with a personal computer.
Figure 4:
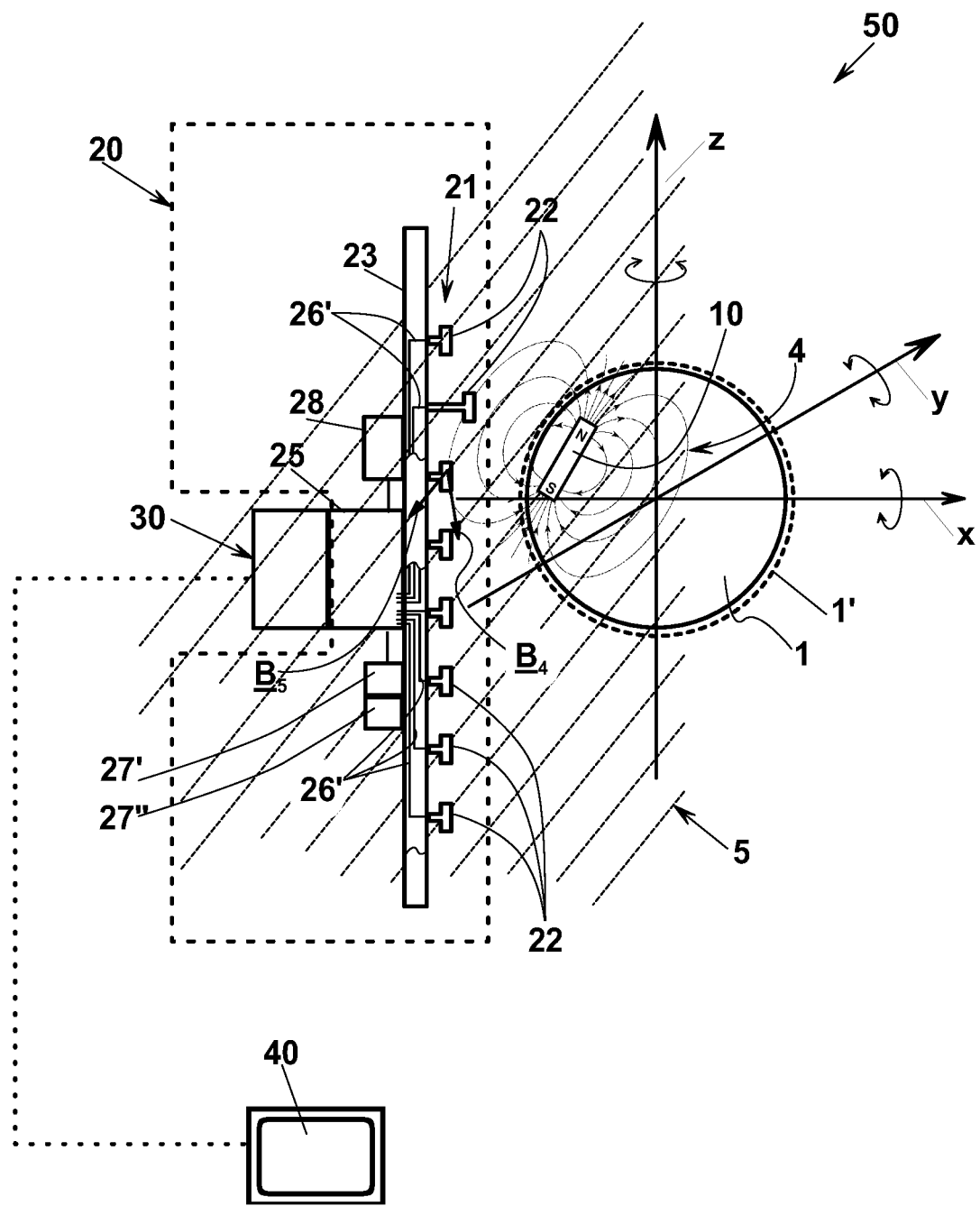
FIG. 4 diagrammatically shows a system according to an exemplary embodiment of the invention, in which the data processing unit is integral to the support of the data collection unit.

As shown in FIGS. 3 and 4, sensor control unit 25 can be implemented with a microcontroller 25 integral to support 23 or arranged on support 23. For instance, the microcontroller can be a PIC18F47J53 type by Microchip, or other type having an appropriate number of digital input ports to provide the independent buses required by the number of sensors, and that has USB port or an equivalent port for connecting remote data processing unit 30, as described hereinafter. Still as an example, the chip comprising sensors 22 can be a Isentek IST8308 type.

As diagrammatically shown in FIG. 4, data processing unit 30 can also be integral to support 23 of data collection unit 20, and can have a connection to an operator interface 40, such as a display or a monitor 40. Alternatively, as diagrammatically shown in FIG. 3, data processing unit 30 can be implemented with a calculation device out of the data collection unit, for example a personal computer 30 or an equivalent device including a conventional operator interface means 33. In the latter case, the connection between sensor control unit 25 and data processing unit 30 can be made by a conventional data transfer means, such as a USB cable 37, which can work also serve as an electric connection means of magnetic sensor control unit 25 and, through the same, of magnetic field sensors 22 and other parts of data collection unit 20, as referred to hereinafter.

The flowsheets of FIGS. 5-8 describe a possible operation mode of magnetic field sensors 22 and of logical magnetic field sensor control unit 25 and of a control unit 30 of the data produced by magnetic field sensors 22.

Figure 5:
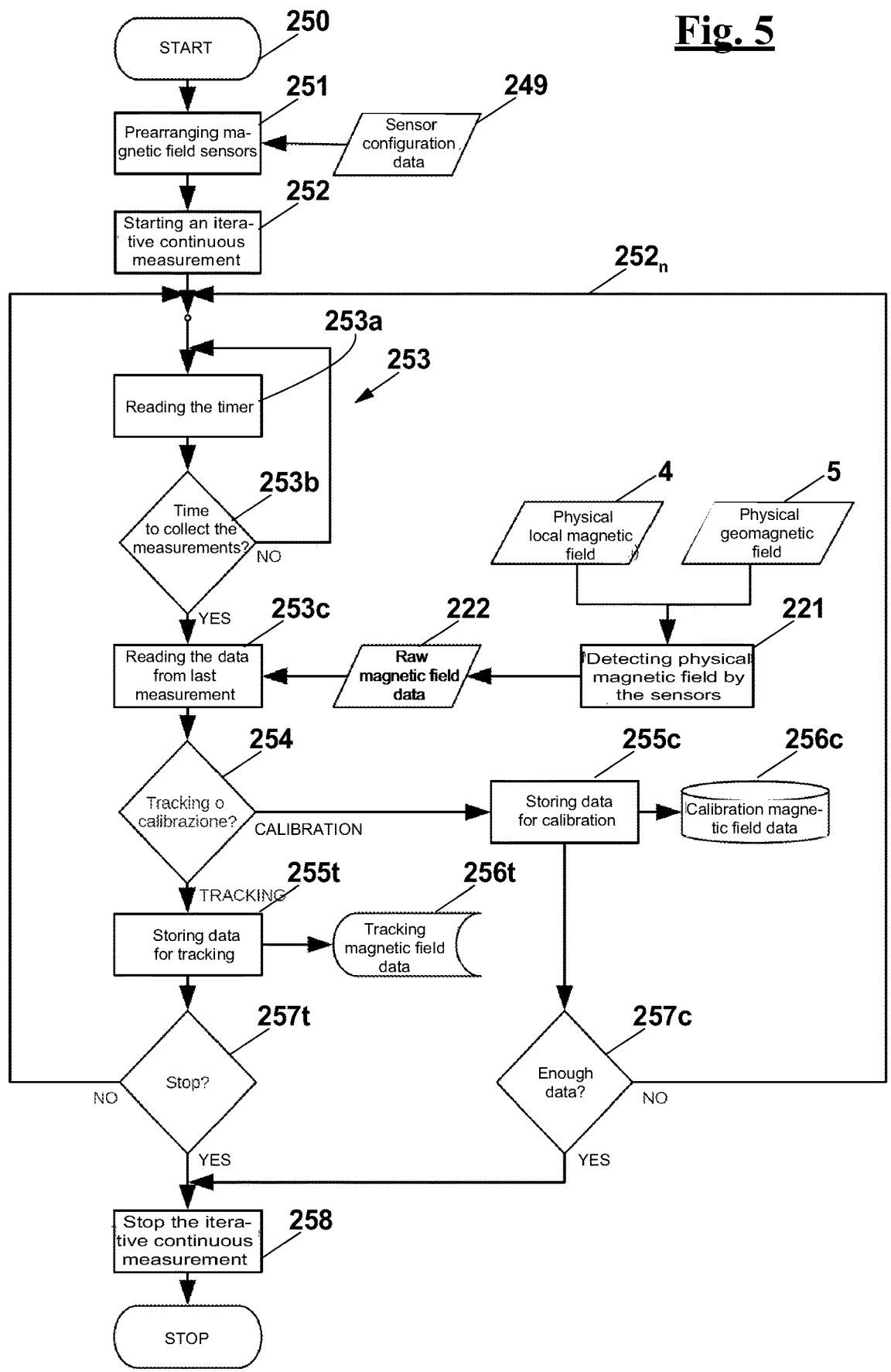
FIG. 5 is a flowsheet of the magnetic field data collection unit.

In particular, with reference to FIG. 5, magnetic sensor control unit 25, once it has received a data collection start command 250 from an operator, performs a step 251 of prearranging magnetic field sensors 22 according to configuration data 249 stored in a memory unit of the collection unit and, subsequently, starts an iterative continuous measurement step 252 comprising a plurality of identical measurement cycles 252$_n$, where n is a subscript counting the measurement cycles, each of said cycles including a sequence of steps or events as described hereinafter. The data collection start command 250 can be input by the operator in tracking mode or in calibration mode.

Once measurement step 252 has been started, sensors 22 perform a step 221 of detecting the magnetic induction vector at respective detection points, which is the resultant of the contribution of magnetic induction vector $B_4$ of local magnetic field 4, generated by magnetic field source 10, and of magnetic induction vector $B_5$ of geomagnetic field 5 (FIG. 1). The detection step 221 outputs a set of raw magnetic field data 222. These data are indicated this way because they are normally affected by offset and/or gain anisotropy issues, including such particular problems as offset and/or gain inhomogeneity of the sensors, offset and/or gain dependance on the temperature, inhomogeneous gain of the scalar components in the case of vector sensors. These effects can be more or less important, according to the type of sensor in use.

Sensor control unit 25 performs a step 253 of sampling raw magnetic field data 222 each time 253$_b$/YES an interval expires of a plurality of time intervals of predetermined duration stored in a timer 253$a$. Upon each expiration of these time intervals, a step 253$_c$ is performed of reading the lastly measured raw magnetic field data 222.

Once sensor control unit 25 has obtained the new sample of raw magnetic field data 222, sensor control unit 25 performs a step 254 of checking whether the start command has been input in "calibration" mode or in "tracking" mode.

In the first case, sensor control unit 25 performs a step 255$_c$ of storing the current magnetic field datum 222 in a memory unit 27' (FIGS. 3 and 4) of collection unit 20 as a datum of a plurality of calibration magnetic field data 256$_c$, i.e. magnetic field data intended for computing conversion parameters for normalizing raw magnetic field data 222 collected during subsequent uses of the system in tracking mode. It is assumed that, during the step of calibration, magnetic field data 222 are detected and collected while repeatedly modifying the orientation in the space of the array of sensors 22, i.e. the orientation in the space of support 23 and, therefore, of collection unit 20. Memory unit 27' can be, in particular, an EEPROM memory unit, For each datum stored into memory unit 27', sensor control unit 25 performs a step 257$_c$ of checking whether the stored data are sufficient or not, in comparison to a predetermined minimum amount of data. If not, a new measurement cycle 252$_n$ is repeated while, in the opposite case, sensor control unit 25 performs a step 258 of discontinuing continuous detection 221 by magnetic field sensors 22 and measurement cycles 252$_n$.

Reverting to checking step 254, if the start command was input in "tracking"

mode, sensor control unit 25 performs a step 255$_t$ of storing current raw magnetic field datum 222 as tracking magnetic field datum 256$_t$ into a memory unit 27" (FIGS. 3 and 4) of collection unit 20 that has the structure of a "first in first out" (FIFO) buffer.

For each datum stored into FIFO buffer 27", sensor control unit 25 performs a step 257$_t$ of checking whether a tracking-stop command has occurred, In particular, input by the operator. If not, If not, a new measurement cycle 252$_n$ is repeated while, in the opposite case, sensor control unit 25 performs a step 258 of discontinuing continuous detection 221 by magnetic field sensors 22 and measurement cycles 252$_n$.

FIG. 6 shows the operations carried out by data processing unit 30 when operating in "calibration" mode. Data processing unit 30 is configured to perform a process of computing conversion parameters 310 starting from a set of calibration raw magnetic field data 256$_c$, available in memory unit 27' of sensor control unit 25, as described above (FIG. 5), and recovered by data processing unit 30 through a step 301 of reading memory unit 27'.

For example, if $V_{j,n}$ indicates the values of the component oriented as the $j^{th}$ axis of 3 coordinate axes in a $n^{th}$ of N stored data, the process comprises a step 302 of calculating a matrix $T_{i,j}^{(k)}$ of gain-related parameters and an offset vector $O_j^{(k)}$ that minimize the amount:

$$f = \Sigma_{i,j,k,n} = [B_0^2 - (T_{i,j}^{(k)} V_{j,n} - O_j^{(k)})^2]^2 \qquad [1]$$

where each value of $k=0 \ldots (K-1)$ relates to a respective magnetic field sensor 22, K is the total number of sensors in use of array 21, i is a further subscript referring to the coordinate axes and $B_0$ is the module of the geomagnetic field that is detected while changing the orientation of array 21 of magnetic field sensors 22, by which the calibration-intended magnetic field data 256$c$ are collected.

In the ideal case that the axes of $k^{th}$ sensor are perfectly orthogonal, the matrix $T_{i,j}^{(k)}$ is a diagonal matrix in which $T_{i,j}^{(k)}=0$ for $i \neq j$, which has therefore only three non-zero coefficients that are the gain correction parameters of $k^{th}$ sensor along the three axes of it. In order to correct possible orthogonality defects of the three axes, for each sensor a step 303 is provided of calculating three further parameters corresponding to the elements of matrix $T_{i,j}^{(k)}$ for which i>j, so that that the matrix T becomes triangular. Finally, assuming that the reference system of array 21 is the one defined by the sensor of subscript k=0, for each sensor of subscript k>0 a rotation matrix $R_{i,j}^{(k)}$ is defined by three angles $\theta^{(k)}$, $\varphi^{(k)}$, $\psi^{(k)}$. These further conversion parameters can be determined by minimizing the amount:

$$g = \Sigma_{i,j,n} (B_{i,n}^{(k)} - R_{i,j} B_{j,n}^{(0)})^2. \qquad [2]$$

The process briefly described above makes it possible to determine nine conversion parameters for each magnetic field sensor 22, i.e., three offset $O_j^{(k)}$, three gain values $T_{i,j}^{(k)}$, and three orthogonality defect compensation coefficients $R_{i,j}$, besides angles $\theta^{(k)}$, $\varphi^{(k)}$, $\psi^{(k)}$, i.e. matrix $R^{(k)}$, for all the sensors with k>0.

In summary, by the analysis of calibration data a set of 12K-3 conversion parameters 310 is generated. A step follows of storing or saving 304 offset vector $O_j^{(k)}$, matrix $T_{i,j}^{(k)}$ of the gain-related parameters, and rotation matrix $R_{i,j}^{(k)}$ for each sensor k. The two matrix $R^{(k)}$, $T^{(k)}$ are indicated in the compact form of a conversion matrix $C(k)=R^{(k)}T^{(k)}$. This way, conversion parameters are available for subsequently normalizing or converting tracking raw magnetic field data 256$_t$ (FIG. 5) into normalized data.

With reference to FIG. 7, once magnetic field data processing unit 30 has received a tracking-mode start command from an operator, magnetic field data processing unit 30 starts a continuous and iterative processing step 320 through sensor control unit 25, said step comprising a plurality of identical measurement cycles 320$_n$, with n is a subscript counting the processing cycles, each of said cycles including a sequence of steps or events as described hereinafter.

Data processing unit 30 firstly performs a step 310 of recovering conversion parameters calculated starting from calibration magnetic field data 256$_c$ and then stored, as previously described (FIG. 6), and a step 324 of reading tracking raw magnetic field data 256$_t$ (FIG. 5) from buffer 27". During the tracking process, sensor control unit 25 and data processing unit 30 can be working at the same time, in other words data processing unit 30 can receive tracking magnetic field data 256$_t$ as these are provided by sensor control unit 25 of collection unit 20, as described above.

Once data processing unit 30 has received conversion parameters 310 and tracking magnetic field data 256$_t$, data processing unit 30 performs a step 325 of normalizing tracking magnetic field data 256$_t$, i.e. a step of converting the latter from raw magnetic field data to normalized and homogeneous magnetic field data 326, using conversion parameters 310, in order to correct the errors due to offset and/or gain inhomogeneity between a sensor and the other, and to gain anisotropy, by which data 256$_t$ are more or less affected, according to sensor type in use and to possible orthogonality defects of the three axes of the scalar sensors of each vector sensor 22.

Once data processing unit 30 has obtained normalized magnetic field data 326, i.e. the values of the components of magnetic induction vector B at the measurement point of each magnetic field sensor 22, substantially free from the above described errors and all referred to the coordinate system associated with the sensor of index k=0, and once it has performed a step of recovering position data 331 of sensors 22, data processing unit 30 can use normalized magnetic field data 326 to carry out a step of tracking or a tracking 327.

To this purpose, data processing unit 30 is configured to perform a best-fit optimization process, in which a vector of position coordinates is calculated which minimizes the estimation error, i.e. the distance between the values of expected magnetic field $B_{theo}$ at the positions of sensors 22 and the values of measured magnetic field $B_{msrd}$, i.e. obtained from normalized magnetic field data 326.

The values of magnetic field $B_{theo}$ provided at the positions of sensors 22 can be calculated by adding calculated expected values of local magnetic field 4 and of geomagnetic field 5. The expected values of said local magnetic field 4 can be calculated starting from first guess values of the location and orientation coordinates of magnetic field source 10, schematized as a magnetic dipole or as a combination of magnetic dipoles whose magnetic moment can be obtained by well-known relationships providing the magnetic induction vector generated by a dipole at a known position with respect to it. The expected values of said geomagnetic field at the positions of said magnetic field sensors 22 can be calculated starting from orientation coordinates of said geomagnetic field 5.

For example, the estimation error can be calculated as the sum, hereafter indicated as "S", extended to all magnetic field sensors 22 of array 21 and to the three cartesian directions, of the square of the differences between the measured components and the estimated components of magnetic induction vector $\underline{B}$:

$$S = \sum_{i=1}^{3} \sum_{k=1}^{K-1} \left(B_{i,msrd}^{(k)} - B_{i,theo}^{(k)}\right)^2$$

where $B_{i,msrd}^{(k)}$ is the $i^{th}$ component of the magnetic induction vector measured by the $k^{th}$ of K triaxial sensors, and $B_{i,theo}^{(k)}$ is the $i^{th}$ component of the magnetic induction vector expected at the $k^{th}$ sensor, where the distance between the two vectors magnetic induction is the distance induced by the Euclidean norm, therefore the quadratic distance is minimized. When this error falls below a predetermined value, the coordinates of the current iteration are assumed as the coordinates of dipole 10 and of geomagnetic field 5.

Tracking data 330 generated during the tracking step 327 can be used immediately to carry out a step 332 of updating the control display 40 of the data processing unit, for example a monitor 40 (FIGS. 1, 3, 4), or can be used for a later display, once all the cycles $320_m$ of processing step 320 have been executed.

Once a tracking datum or a block of tracking data 330 has/have been calculated and displayed and/or recorded, data processing unit 30 performs a step 333 of checking whether a processing-stop condition has occurred or not, typically input by an operator. If not, a new processing cycle $320_m$ is repeated, while in the opposite case data processing unit 30 discontinues processing step 320.

The flowsheet of FIG. 8 also relates to the operation of data processing unit 30 to track object 1. In an exemplary embodiment, before starting the continuous and iterative processing step 320, a preliminary step 321 of filling a vector 322 of location and orientation coordinates of dipole 10 as well as of orientation coordinates of geomagnetic field 5 with first guess values for the best-fit calculation process of the tracking step 327, mentioned above with reference to FIG. 7. Coordinate vector 322 is used in the first iteration n=1 of the calculation process of tracking step 327, while in the subsequent iterations n>1 values $329_n$ are used as calculated in the iteration immediately before.

In particular, normalization or conversion step 325 can have the structure described hereinafter, in the light of what has been said above about the way to calculate conversion parameters 310. In a first calculation step $325_a$, the $i^{th}$ component $B^{(k)}_{i,n}$ of magnetic induction vector at the $k^{th}$ sensor in the $n^{th}$ measurement, i.e. in the $n^{th}$ collection cycle of FIG. 5, is calculated starting from the corresponding raw value $V_{j,n}$ as:

$$B_{i,n}^{(k)} = \Sigma_j T_{i,j}^{(k-opt)}(V_{j,n} - O_j^{(k-opt)}) \quad [3]$$

where $O_j^{(k-opt)}$ is the offset vector, according to the three coordinate axes j=0 . . . 3 of the $k^{th}$ sensor, and $T_{i,j}^{(k-opt)}$ is the matrix for correcting the errors due to gain variability of the $k^{th}$ sensor, $O_j^{(k-opt)}$ and $T_{i,j}^{(k-opt)}$ being the values of $O_j^{(k)}$ and $T_{i,j}^{(k)}$, respectively, minimizing the amount [1] calculated in the step of computing the conversion parameters.

This passage makes it possible to remove the offsets and to make the magnetic field measurements isotropic. The normalization is advantageously completed by a further algebraic step consisting in applying the rotation matrix Rid to above obtained values $B^{(k)}_{i,n}$, the rotation matrix being calculated in a subsequent calculation step $325_b$ by minimizing the amount [2] and defined by three angles $\theta^{(k)}$, $\varphi^{(k)}$, $\psi^{(k)}$.

In particular, in the case of the magnetoresistive sensors, the offset and the gain sensitively depend on the temperature. This means that the conversion parameters calculated at a given temperature are normally not suitable for normalizing magnetic field data read when the sensors have a different temperature. In order to assist the operator in the decision whether to ask the apparatus to carry out a step of computing new conversion parameters to be used for normalizing the magnetic field data in subsequent data collection and processing, in an exemplary embodiment, collection unit 20 comprises a sensor, not shown, for measuring the actual temperature at which magnetic field sensors 22 operate. Magnetic field sensor control unit 25 is configured to detect this actual temperature, for instance, when a data acquisition start command 250 is received, and before performing step of prearranging magnetic field sensors (FIG. 5). Magnetic field sensor control unit 25 is also configured to calculate the difference between the actual temperature and the temperature at which the last calibration has been made and, if this difference is higher than a predetermined value, for emitting an alarm signal and, preferably, a request message asking whether to calculate new conversion parameter or not.

In the case of a system 50 according to the exemplary embodiment of FIG. 3, in which the data processing unit is implemented with such a device as a personal computer remote from data collection unit 20, collection unit 20 advantageously comprises a housing 28 for an internal battery for electrically supplying sensor control unit 25 and magnetic field sensors 22, in particular during the calibration step, in particular during the step of computing new conversion parameters. Advantageously, in order to limit battery consumption, sensor control unit 25 is configured to automatically block the electrical supply to collection unit 20 from the internal battery when a calibration stop command is received, in particular, after a predetermined delay time since after receiving the end-of-calibration signal.

For the sake of simplicity, reference has been made till now to the case in which magnetic field source 10 comprises or can be considered a single magnetic dipole 10. However, in an exemplary embodiment, magnetic field source 10 can comprise a plurality of magnetic dipoles rigidly connected to each other or to body 1 so as to be differently oriented in the space. In this case, the position coordinates include:

three spatial location coordinates of magnetic field source 10 with respect to array 21 of magnetic field sensors 22;

three orientation coordinates of magnetic field source 10, and at least two orientation angles of array 21 of magnetic field sensors 22 with respect to geomagnetic field 5.

Figure 9A:
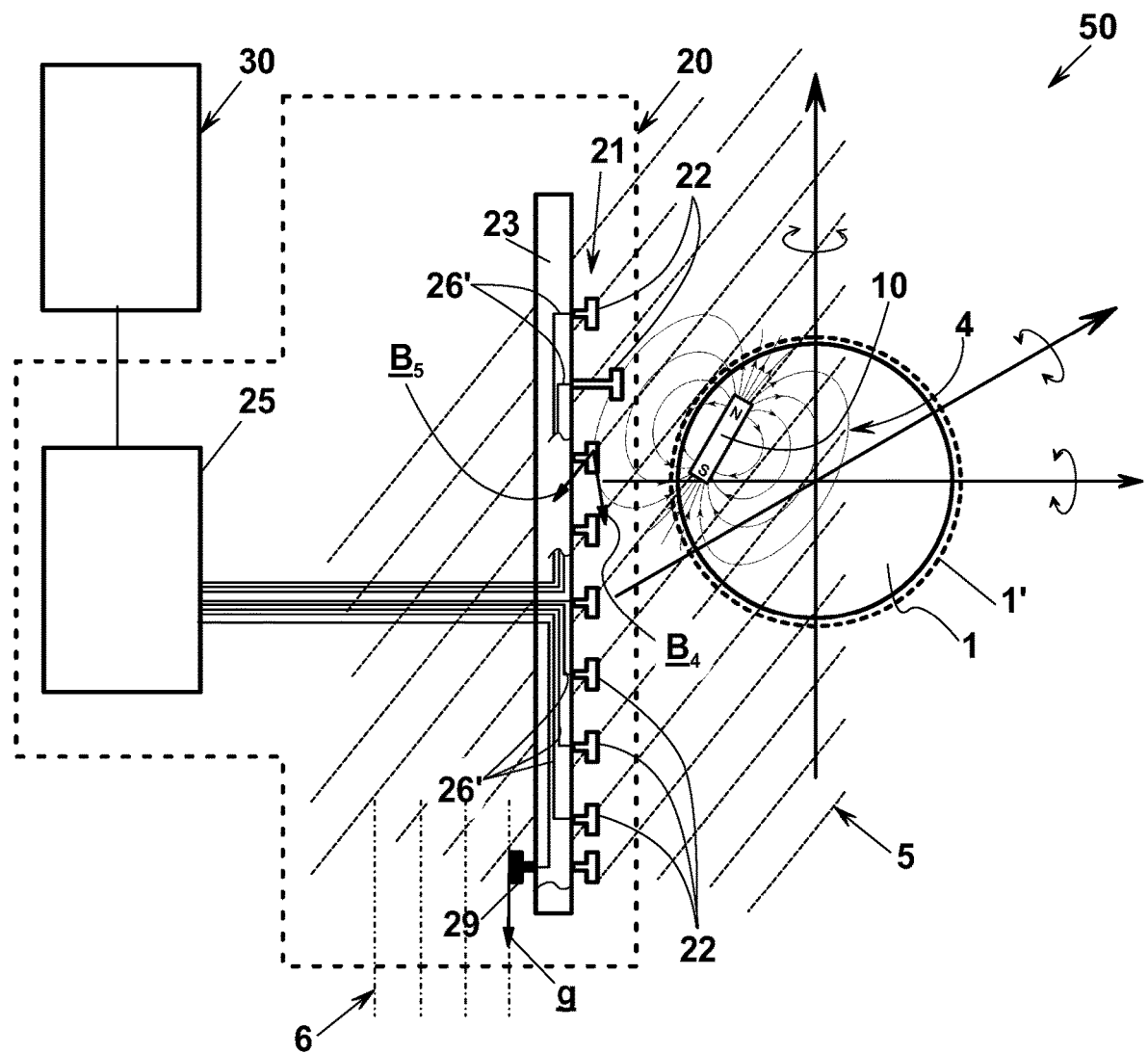
FIG. 9A diagrammatically shows a system according to an exemplary embodiment of the invention, in which a gravimetric sensor is also provided in the collection unit.

Regardless the above, in another exemplary embodiment, as diagrammatically shown in FIG. 9A, collection unit 20 can comprise, in addition to magnetic field sensors 22, also a gravimetric sensor 29, preferably mounted to support 23. In this case, gravimetric sensor 29 makes it possible to know the orientation of the gravitational field g with respect to support 23 and to array 21 of magnetic field sensors 22. In this exemplary embodiment, the position coordinates include:

three spatial location coordinates of magnetic field source 10 with respect to array 21 of magnetic field sensors 22, at least two orientation coordinates of magnetic field source 10, and three coordinates of geomagnetic field 5, so that a complete information is provided, including three angles of array 21 with respect to the gravitational field 6.

Figure 9B:
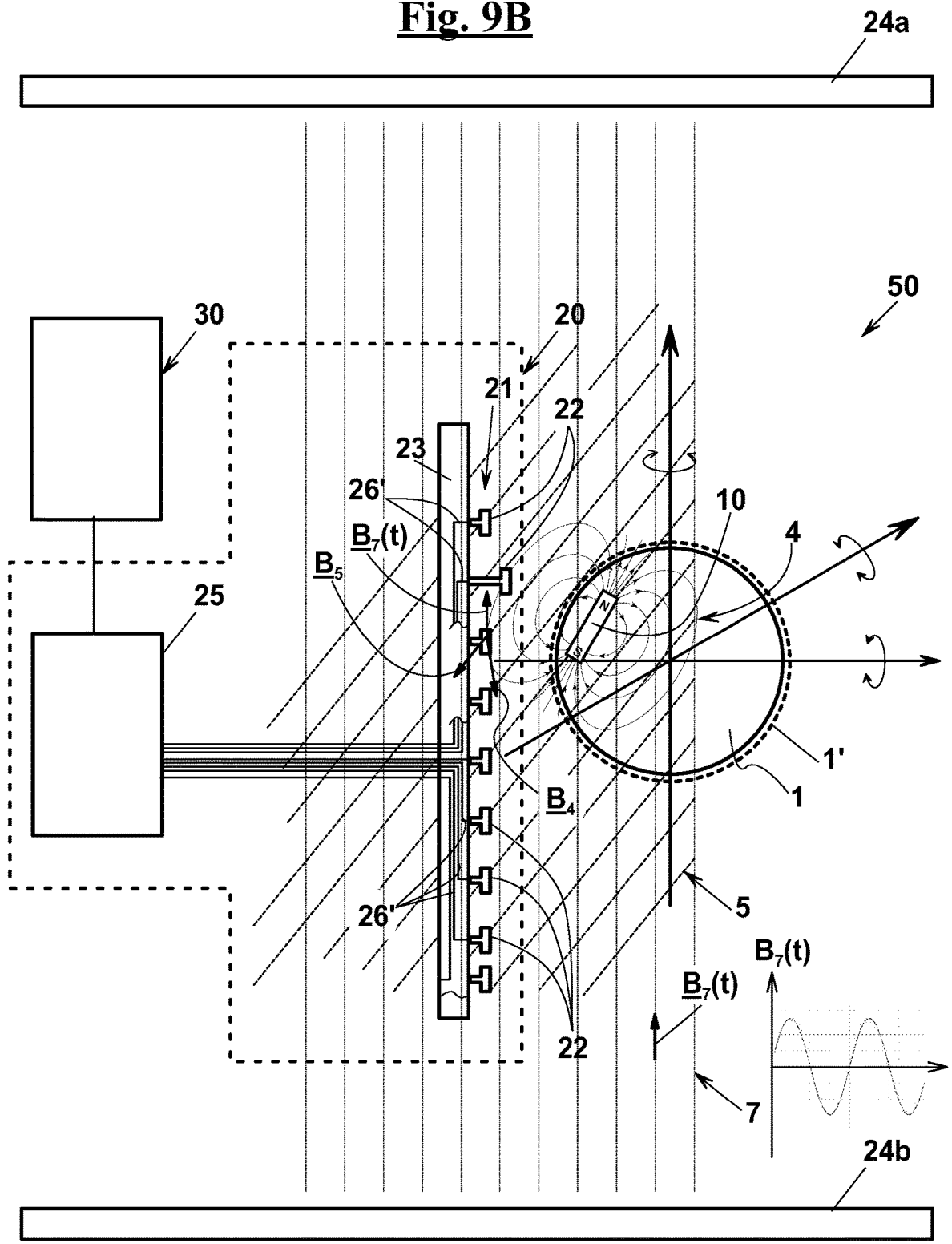
FIG. 9B diagrammatically shows a system according to an exemplary embodiment of the system, in which a magnetic field generator device is provided for generating an auxiliary magnetic field variable with time.

In an alternative exemplary embodiment, diagrammatically shown in FIG. 9B, system 50 can comprise a device 24 to generate an auxiliary magnetic field 7 whose magnetic induction vector $\underline{B}_7$ has a direction that is different from the direction of magnetic induction vector $\underline{B}_6$ of geomagnetic field 6, and a module $B_7$ that changes with time in a known way, for instance, it changes sinusoidally with time. The generator device can include, for instance, a pair of induction coils 24a and 24b, arranged opposite to each other with respect to support 23 and to the subject wearing the same.

In particular, in the not limitative example shown in Fig., auxiliary magnetic field 7 is a homogeneous field whose field lines are not parallel to the field lines of geomagnetic field 6. In this case, in order to obtain a substantially homogeneous auxiliary magnetic field, induction coils 24a, 24b are parallel to each other and have a diameter larger than a minimum predetermined value.

In this exemplary embodiment, the position coordinates include:
three spatial location coordinates of magnetic field source 10 with respect to array 21 of magnetic field sensors 22,
at least two orientation coordinates of magnetic field source 10, and
three coordinates of geomagnetic field 5,
so that a complete information is provided, including three angles of array 21 with respect to a system integral to the environment, and univocally determined with respect to the directions of geomagnetic field 5 and of $\underline{g}$, i.e. of geomagnetic field 5 and of auxiliary magnetic field 7.

Figure 10:
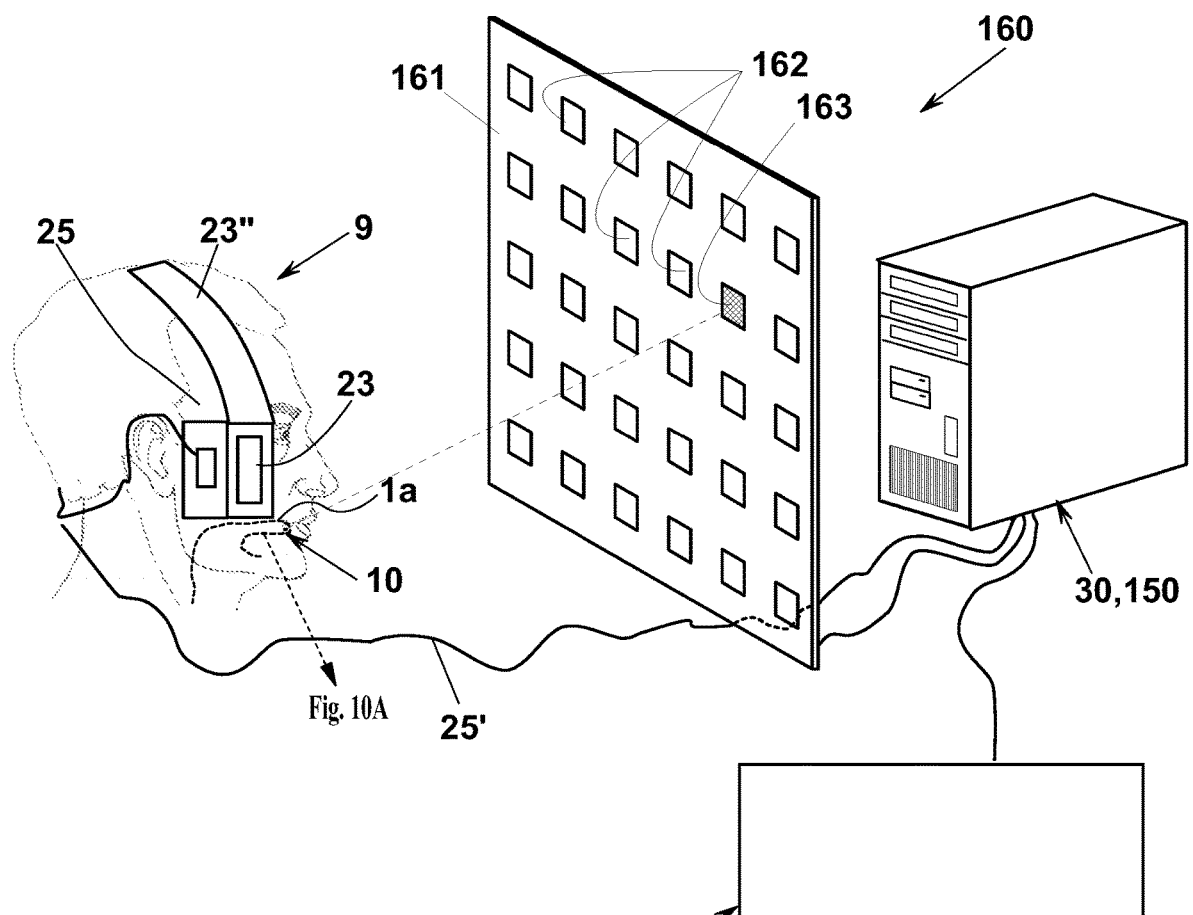
Figure 10A:
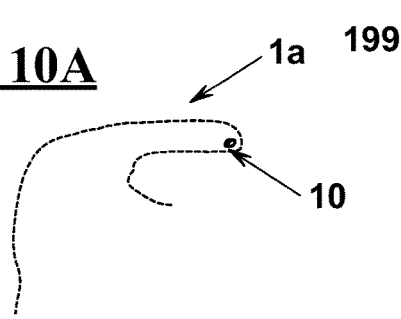
Figure 11:
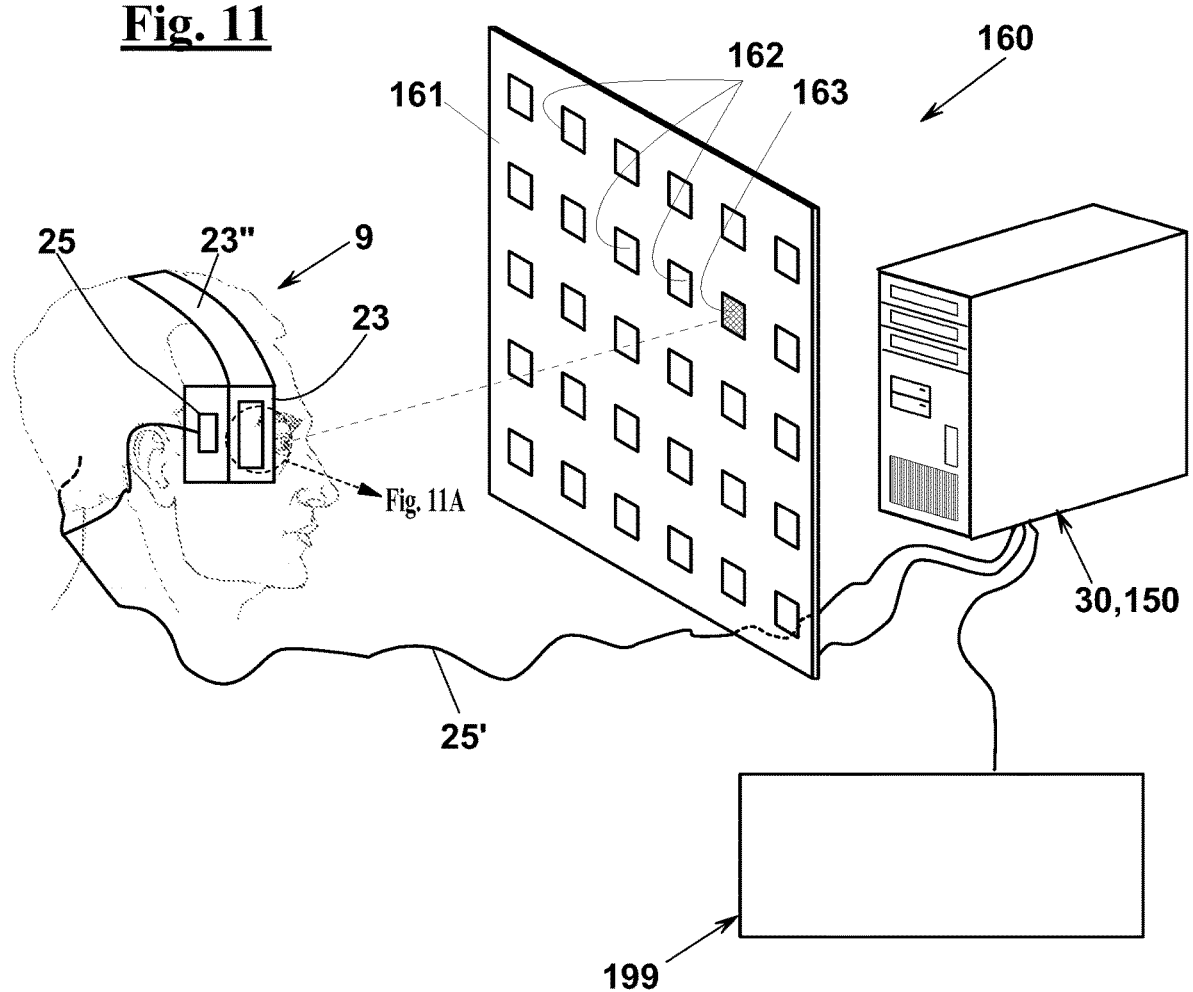
Figure 11A:
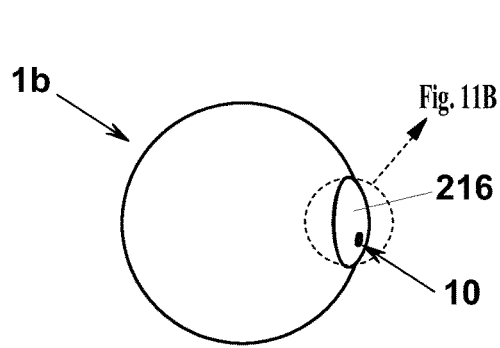
Figure 11B:
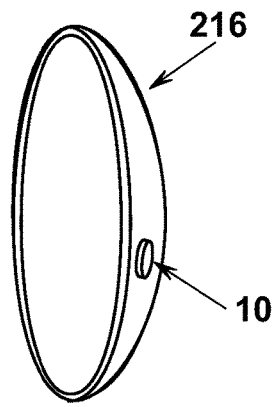

With reference to FIGS. 10-11B, as an application of system 50 according to the invention, apparatuses 100, 200 are described for tracking a subject's tongue 1a and a subject's eyeball or eyeballs 1b, respectively, in order to control such a peripheral device 199, 299 as a robotic device and/or a communication device according to the movements of tongue 1a or of eyeball/eyeballs 1b. In these apparatuses, support 23 is configured to be fixedly worn on the subject's head 9, in an appropriate position with respect to tongue 1a or eyes 1b, preferably in a lateral position with respect to the subject's head 9. The magnetic field source is a small, preferably of cylindrical magnet 10, configured to be fixed to tongue 1a (FIG. 10A) or to the subject's eyeball/eyeballs 1b (FIG. 11A), respectively. In the latter case, the size of magnet 10 does not preferably exceed Ø3 mm×1 mm, in order to be easily incorporated into a contact lens 216 (FIG. 11B).

Apparatuses 100, 200 include an interface and command device 150 between system 50 and peripheral device 199. Interface and command device is configured to receive the position coordinates of magnetic field source 10 with respect to geomagnetic field 5 from data processing unit 30 of system 50, and to interpret these parameters as a pointing direction of tongue 1a or eyeball 1b towards an icon 163 selected among the icons 162 displayed on a panel 161 arranged in front of the subject, each of which corresponding to a specific command for peripheral device 199. Peripheral device 199 can also be a word processor device incorporated in the interface and command device. Preferably, interface and command device 150 is also configured to show the icon 163 selected by the subject, in order to confirm that the latter has selected the right command on panel 161 by the tongue or gaze direction.

In particular, interface and command unit 150 can be incorporated in a personal computer 160 or in an equivalent device, such as a tablet or a smartphone. More in particular, if data processing unit 30 of tracking system 50 is implemented with a personal computer or with an equivalent device, both data processing unit 30 of system 50 and interface and command unit 150 can be resident in a same computing machine 160.

In particular, apparatus 100 can comprise a sound detector, not shown, connected to the interface and control unit 150, which comprises a means for recognizing subject's verbal communication act, and is configured to discontinue the generation of control signals through panel 161 when subject's verbal communication is recognized.

Figure 12:
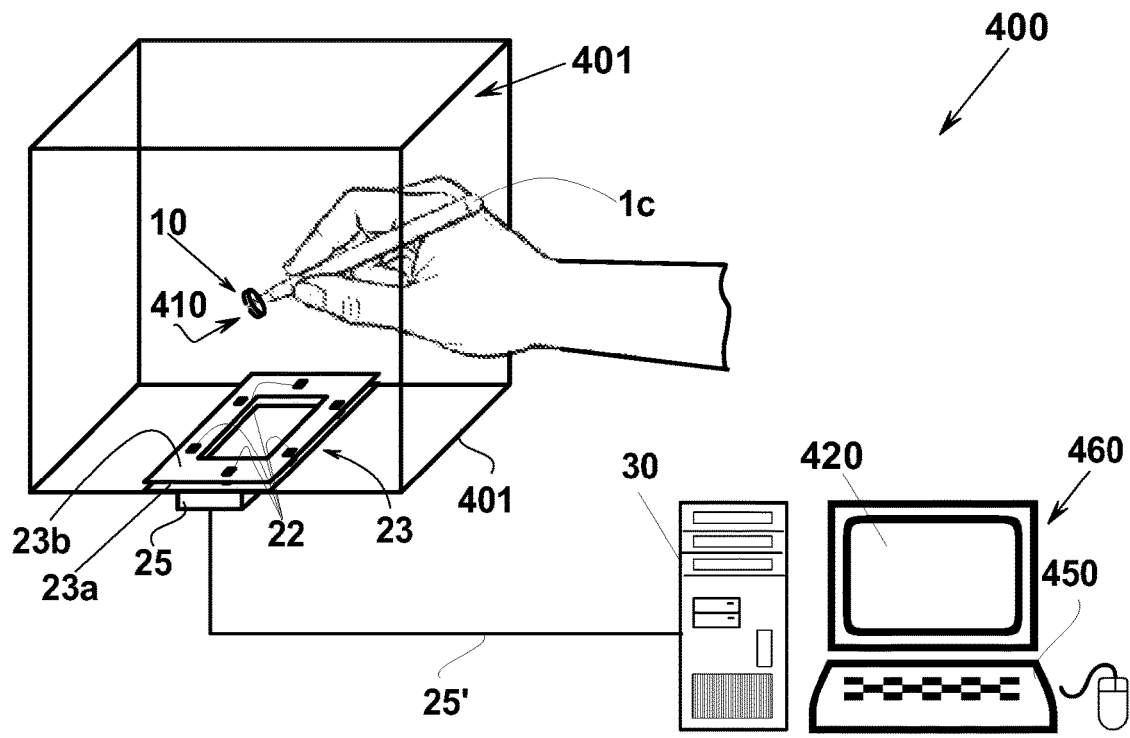

With reference to FIG. 12, as a further application of system 50, a three-dimensional pointing apparatus 400 is described, in particular a three-dimensional writing device. The pointing apparatus 400 comprises a fixed three-dimensional drawing pad 401, i.e. a drawing box 401 suitable for performing in 3D the functions performed in 2D by a conventional drawing pad, the three-dimensional drawing pad reproducing a drawing environment or command environment. The pointing apparatus 400 also comprises a pointing device 1c such as a pen a tip portion 410 of which is configured to be displaced in the three-dimensional drawing pad 401, as well as a interface and command device 450 that, in particular, can be incorporated in a personal computer 460 or in an equivalent device. More in particular, if data processing unit 30 of tracking system 50 is implemented with a personal computer or with an equivalent device, both data processing unit 30 and interface and command device 450 can be resident in a same computing machine 460. Interface and command device 450 is configured to display graphic elements on a display unit 420, responsive to the position and/or to an active/inactive status of pointing device 1c in the three-dimensional drawing pad 401. Display unit 420 can comprise the monitor of personal computer 460. In a preferred alternative, since the tracker generates a three-dimensional information, display unit 420 can comprise a VR viewer. In this case, magnetic field source 10 is preferably arranged at tip portion 410 of pointing device 1c, and support 23 is integral to the three-dimensional drawing pad 401, or even incorporated therein.

Figure 13:
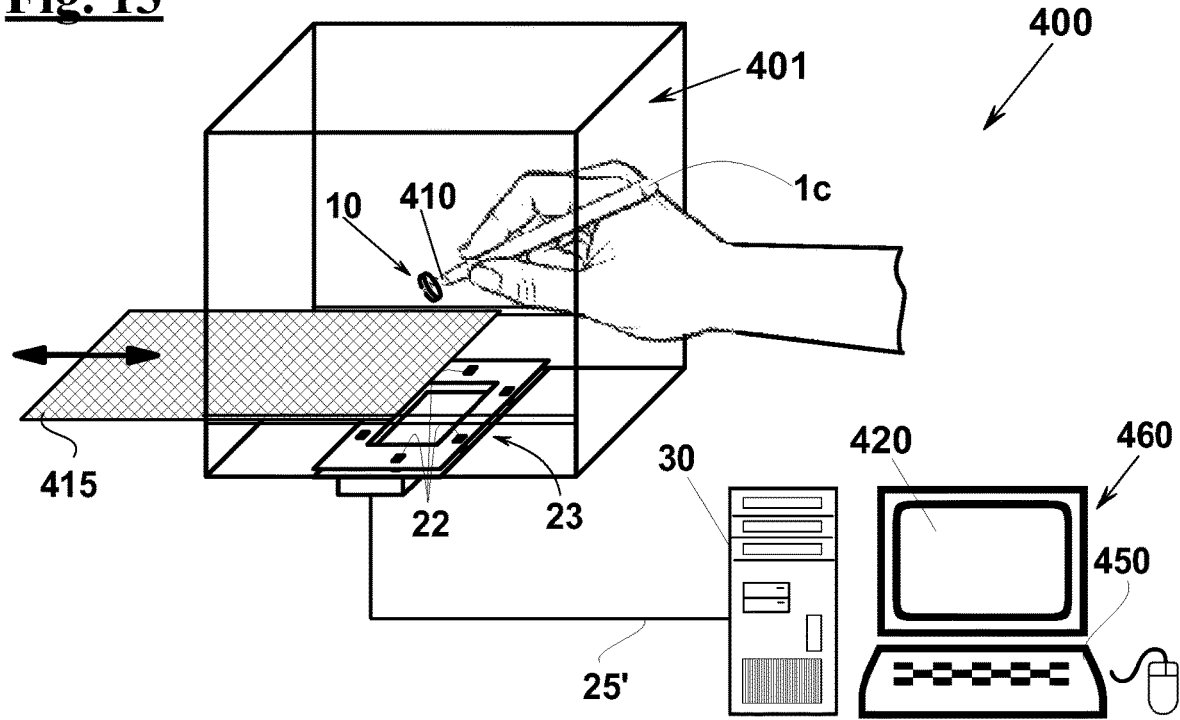

With reference to FIG. 13, optionally, the three-dimensional pointing apparatus 400 can also comprise a shield element 415 made of a ferromagnetic material arranged for performing a relative movement with respect to a movement field of portion 410 of pointing device 1c at which magnetic field source 10 Is fixed. This way, magnetic field source 10 can be shielded in a variable way with respect to sensors 22. Therefore, tracking system 50, through sensors 22, can appreciate intensity changes of local magnetic field 4, which can be associated to a variation of a display parameter or feature of a graphic element 420. This feature can be, for instance, even in a selective way, a line thickness, a line or picture color or color tonality, a line or picture hatch density as shown in display unit 420.

In an exemplary embodiment, not shown, the shield element is contained in the pen-like element, in particular in a tip portion of the pen-like element, and the pen-like element has a device for driving said movement accessible to the hand of a user.

Figure 14:
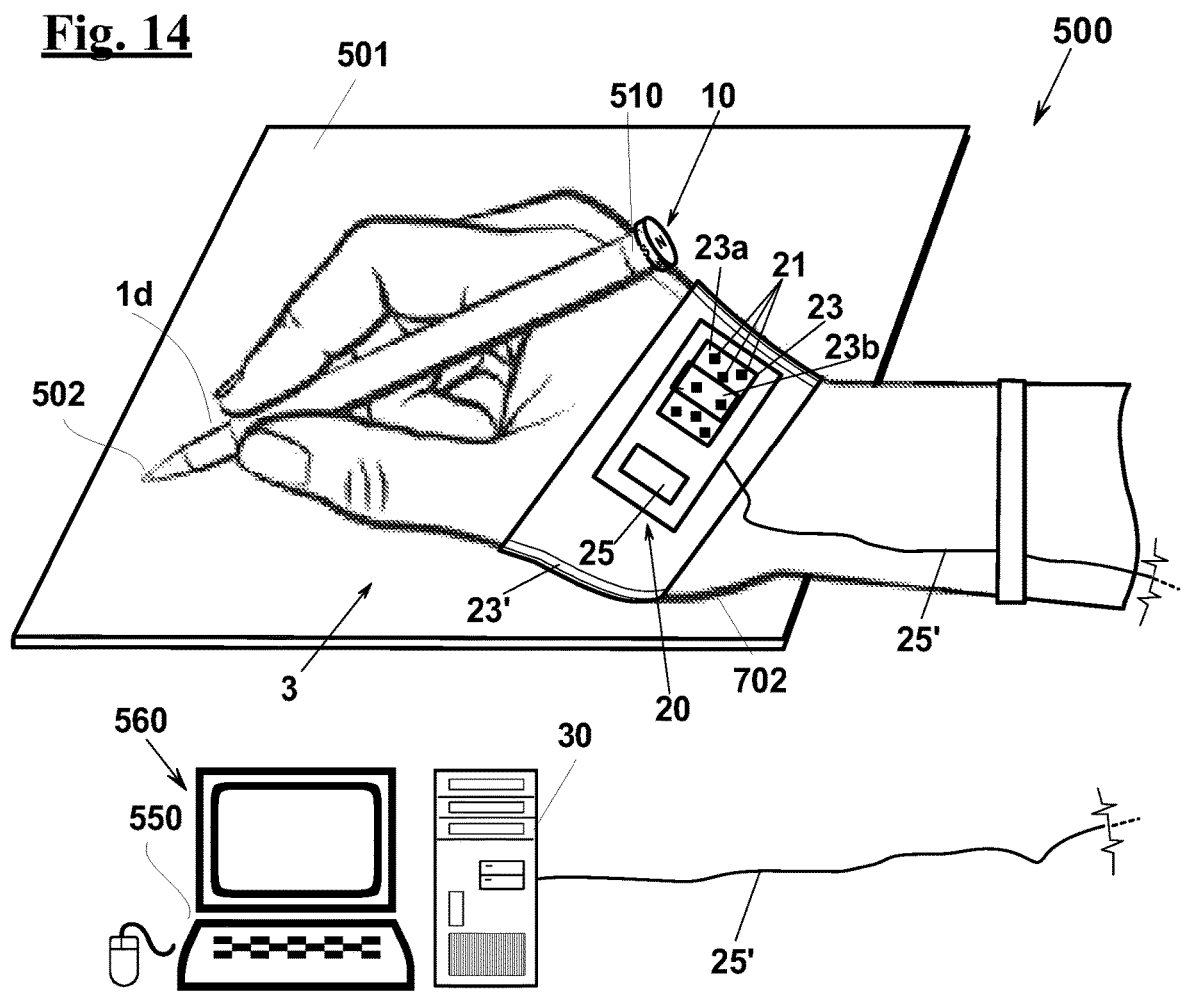

With reference to FIG. 14, as a further application of system 50, an apparatus 500 is described for measuring a subject's graphometric features, in particular an apparatus for checking the authenticity of a subject's signature, or for investigating implications physiologic, and even pathologic aspects of some features of a subject's handwriting. Apparatus 500 comprises a pen-like element, for example a pen 1d, and a surface 501 configured to feel the contact of pen tip 502 on surface 501. Apparatus 500 also comprises an interface and command device 550 that, in particular, can be incorporated in a personal computer 560 or in an equivalent device. More in particular, if data processing unit 30 of tracking system 50 is implemented with a personal computer or with an equivalent device both data processing unit 30 and interface and command device 550 can be resident in a same computing machine 560. Interface and command device 550 has a computing means that is associated to sensitive surface 501 for associating a plurality of graphometric features to a writing contact of pen-like element 1*d* on surface 501.

In particular, magnetic field source 10 is arranged at a pen-like element portion 510 different from tip 502, for example at an end portion of the pen-like element opposite to the tip portion, while support 23, with the array of magnetic field sensors 22, is configured to be fixed to the palm 702 of a hand 3, for example by means of a belt 23'. In this case, the graphometric features comprise two inclination angles of pen-like element 1*d* during the writing contact, and also the inclination of hand 3 in a reference system external to apparatus 500. In an alternative, not shown, support 23 is integral to sensitive surface 501, in which case the graphometric features comprise two inclination angles of pen-like element 1*d* during the writing contact.

In a further application, not shown, of system 50, an apparatus for tracking displacements of a surgical tool 1*e* in a patient's body, comprises the system according to the previous description, in which magnetic field source 10 is arranged at a portion of the surgical tool, in particular at a tip portion thereof, while support 23, with array 21 of magnetic field sensors 22, is configured to be fixed, for instance, to a surgeon's arm of, or to a support at the operating bed.

Figure 15:
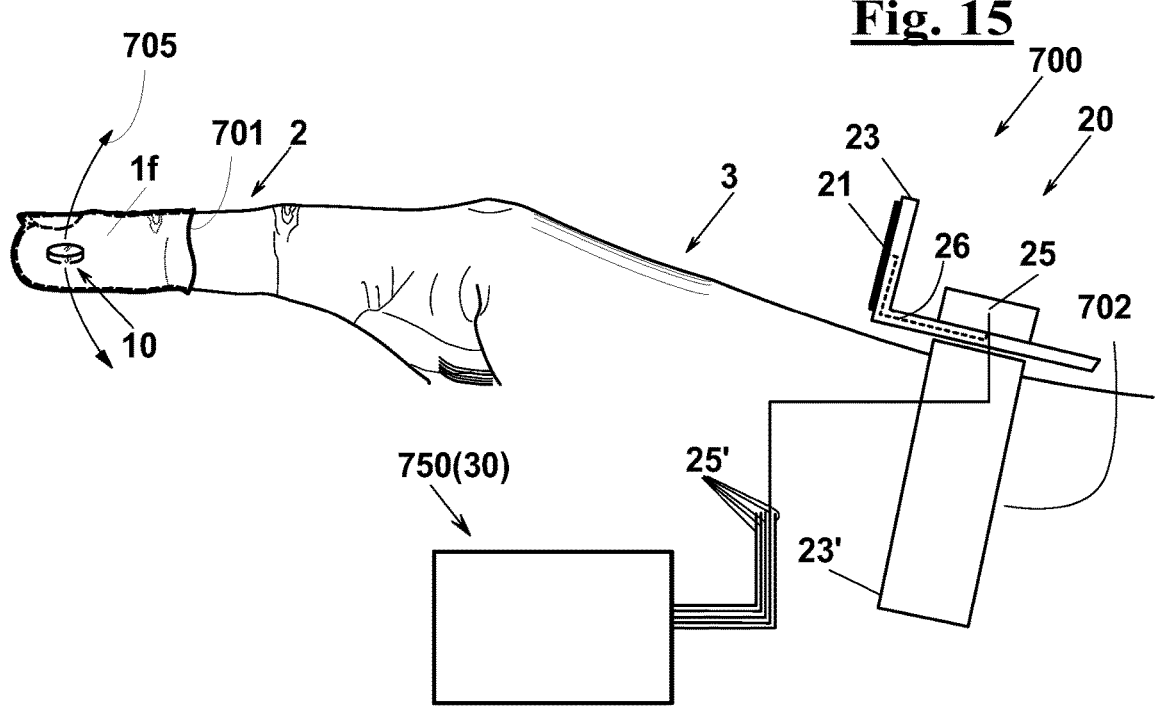

With reference to FIG. 15, as a further application of system 50, an apparatus for tracking displacements 705 of the fingers 2 of a subject's hand 3, comprises at least one system according to the previous description, in which magnetic field source is arranged at a portion 1*f* of a respective finger 2 of hand 3, in particular at a phalanx 1*f*. For instance, the magnetic field source, in the form of a magnet 10, can be incorporated in a thimble 701. Support 23, with array 21 of magnetic field sensors, is configured to be fixed to the wrist 702, as shown in the figure or, in an alternative not shown, to the corresponding subject's forearm, in both cases, for example, through a bracelet 23'. An interface and command device 750 can be provided for receiving the tracking data of fingers 2, and can comprise data processing units 30 of respective devices 50 for tracking respective fingers 2 of hand 3, connected to respective sensor control units 25 through respective connection cables 25'.

The foregoing description of exemplary embodiments of the invention will so fully reveal the invention according to the conceptual point of view, that others, by applying current knowledge, will be able to modify and/or adapt for various applications such embodiment without further research and without parting from the invention and, accordingly, it is to be understood that such adaptations and modifications will have to be considered as equivalent to the specific embodiments. The means and the materials to implement the different functions described herein could have a different nature without, for this reason, departing from the field of the invention. It is to be understood that the phraseology or terminology that is employed herein is for the purpose of description and not of limitation.

The invention claimed is:

1. A system (50) for tracking location and/or orientation displacements of an object (1) in the space, comprising:
 a data collection unit (20) comprising:
  an array (21) of magnetic field sensors (22) fixed at respective predetermined sensor positions on a support (23) and configured to measure magnetic field data, said support (23) configured to be arranged proximate to said object (1);
  a sensor control unit (25) for controlling said magnetic field sensors (22),
  a connection means (26) connecting said magnetic field sensors (22) and said sensor control unit (25), said connection means arranged to transfer said measured magnetic field data by said magnetic field sensors (22) to said sensor control unit (25),
 a magnetic field source (10) comprising at least one magnetic dipole having a magnetic moment and configured to generate a local magnetic field (4) and to be fixed to said object (1), wherein said magnetic field source (10) is arranged to generate said local magnetic field (4), at said positions of said magnetic field sensors, with an intensity set between 5 and 500 microTesla,
 such that said magnetic field sensors (22) detect, besides said local magnetic field (4), also the geomagnetic field (5);
 a data processing unit (30) configured to
  receive said measured magnetic field data from said sensor control unit (25);
  recover position data (331) of said magnetic field sensors (22);
  fill a vector (322) of:
   location and orientation coordinates of said at least one magnetic dipole (10), with respect to said array (21) of said magnetic field sensors (22); and of
   orientation coordinates of said geomagnetic field, (5) with respect to said array (21) of said magnetic field sensors (22) with first guess values;
  calculate, starting from said first guess values of said location and orientation coordinates of said at least one magnetic dipole (10), expected values of said local magnetic field (4) at said positions of said magnetic field sensors (22),
  calculate, starting from said first guess values of said orientation coordinates of said geomagnetic field (5), expected values of said geomagnetic field (5) at said positions of said magnetic field sensors (22);
  calculate expected overall magnetic field values at said sensor positions (22) as a resultant of the contribution of a magnetic induction vector (B4) of said local magnetic field (4) generated by said magnetic field source (10) and of a magnetic induction vector (B5) of said geomagnetic field (5);
  determine, starting from said magnetic field data, a vector of position coordinates comprising:
   location coordinates of said magnetic field source (10) with respect to said array (21) of said magnetic field sensors (22);
   orientation coordinates of said magnetic field source (10) with respect to said array (21) of said magnetic field sensors (22);
   orientation coordinates of said array (21) of said magnetic field sensors (22) with respect to said geomagnetic field (5),
  which minimizes a distance between:
   said expected overall magnetic field values at said sensor positions and
   measured magnetic field values obtained by said magnetic field data,
  wherein said data processing unit (30) is configured to recognize in said magnetic field data contributes of said local magnetic field (4), determined by said location and orientation coordinates of said magnetic field source (10), and of said geomagnetic field (5), determined by said orientation coordinates of said array (21), in order to determine said location and said orientation of said magnetic field source (10) and, therefore, determine a mutual orientation of said magnetic field source (10) and of said magnetic induction vector B5 of said geomagnetic field (5).

2. The system according to claim 1, wherein said data processing unit (30), in order to obtain said vector of position coordinates which minimizes said distance, is configured to:

define increment values for: said location coordinates of said magnetic field source (10); said orientation coordinates of said magnetic field source (10); said coordinates of said geomagnetic field (5);

perform a sequence of steps including the steps of:

calculating said expected values of said local magnetic field (4);

calculating said expected values of said geomagnetic field (5);

calculating said expected values of said overall magnetic field;

calculating said distance;

checking whether said distance is larger than a predetermined target distance;

if said distance is larger than said predetermined target distance, then update said guess values of: said location coordinates of said magnetic field source (10); said orientation coordinates of said magnetic field source (10); said coordinates of said geomagnetic field (5) by increasing each of said guess values by respective said increment values; and repeating said sequence of steps;

if said distance is not larger than said predetermined target distance, then returning said guess values as the tracking values of:

said location coordinates of said magnetic field source (10) with respect to said array (21) of said magnetic field sensors (22);

said orientation coordinates of said magnetic field source (10) with respect to said array (21) of said magnetic field sensors (22);

said orientation coordinates of said array (21) of said magnetic field sensors (22) with respect to said geomagnetic field (5).

3. The system according to claim 2, wherein said data processing unit (30) is also configured to:

if said distance is larger than said predetermined target distance, compare said distance with a value of said distance as calculated in a previous iteration of said sequence of steps;

if said distance is not shorter than a value of said distance as calculated in a previous iteration of said sequence of steps, recover previous guess values from said previous iteration of said sequence of steps, and update said previous guess values by increasing each of them by an amount selected between the corresponding opposite value of the absolute value of said increment value and the absolute value of said increment value;

if said distance is shorter than a value of said distance as calculated in a previous iteration of said sequence of steps, update said guess values by increasing each of them by an amount selected between the corresponding opposite value of the absolute value of said increment value and the absolute value of said increment value;

repeat said sequence of steps.

4. The system according to claim 2, wherein said data processing unit (30) is also configured to:

before checking whether said distance is larger than said predetermined target distance, checking whether an elapsed calculation time and/or a number of operations performed since when said measured magnetic field data have been received by said sensor control unit (25) exceed upper limit values of said calculation time and/or of said number of operations, respectively;

if none of said upper limit values is exceeded, checking whether said distance is larger than said predetermined target distance and then perform the steps of claim 2;

if at least one of said upper limit values is exceeded, repeat said step of filling a vector (322) with different first guess values and then perform the steps as in claim 1 and in claim 2.

5. The system (50) according to claim 1, wherein said magnetic field source (10) comprises a plurality of magnetic dipoles rigidly connected to each other, in particular two magnetic dipoles, and said position coordinates comprise three location coordinates of said magnetic field source (10) with respect to said array (21) of magnetic field sensors (22), three orientation coordinates of said magnetic field source (10) with respect to said array (21) of magnetic field sensors (22) and at least two orientation coordinates of said geomagnetic field (5) with respect to said array (21) of magnetic field sensors (22).

6. The system (50) according to claim 1, wherein said data collection unit (20) comprises a gravimetric sensor (29), and said position coordinates comprise three location coordinates of said magnetic field source (10) with respect to said array (21) of said magnetic field sensors (22), at least two orientation coordinates of said magnetic field source (10) with respect to said array (21) of said magnetic field sensors (22) and three orientation coordinates of said array (21) of said magnetic field sensors (22) with respect to an external reference system that is in turn referred to the directions of said geomagnetic field (5) and of the gravitational field (6).

7. The system (50) according to claim 1, comprising a means (24) for generating an auxiliary magnetic field (7) variable with time, and said position coordinates comprise three location coordinates of said magnetic field source (10) with respect to said array (21) of said magnetic field sensors (22), at least two orientation coordinates of said magnetic field source (10) with respect to said array (21) of said magnetic field sensors (22) and three orientation coordinates of said array (21) of said magnetic field sensors (22) with respect to an external reference system that is in turn referred to the directions of said geomagnetic field (5) and of said auxiliary magnetic field (7).

8. The system (50) according to claim 1, wherein said connection means (26) comprises a plurality of buses (26') independent from each other, each of said buses (26') connecting a respective magnetic field sensor (22) of said magnetic field sensors with said sensor control unit (25), so that said sensor control unit (25) can collect said magnetic field data at the same time from all said magnetic field sensors (22).

9. The system (50) according to claim 8, wherein said magnetic field sensors (22) are triaxial magnetic field vector sensors and said conversion parameters comprise, for each of said magnetic field sensors (22), three offset values, three gain correction coefficients and three orthogonality defect compensation coefficients.

10. The system (50) according to claim 1, wherein said magnetic field sensors (21) are triaxial vector sensors;
said magnetic field source (10) is selected in such a way that a ratio between a linear
dimension of said array (21) of said magnetic field sensors (22) and a linear dimension of said magnetic field source (10) is set between 40 and 60 for a subset of at least three of said vector sensors (21).

11. The system (50) according to claim 10, wherein said linear dimension ratio is about 50.

12. The system (50) according to claim 1, wherein said data processing unit (30) is configured to perform a calibration step comprising the steps of:
receiving calibration-intended magnetic field data (256*c*) obtained from homogeneous magnetic field measurements carried out while changing the orientation in the space of said array (21) of said magnetic field sensors (22);
computing conversion parameters for each of said magnetic field sensors (22), starting from said calibration-intended magnetic field data (256*c*).

13. The system (50) according to claim 1, wherein
said data processing unit (30) is configured to perform a step of calibrating said magnetic field sensors (22);
said data collection unit (20) comprises a temperature sensor of said magnetic field sensors (22),
said sensor control unit (25) is configured to detect an actual temperature of said magnetic field sensors (22) and to:
store a calibration temperature, at which said calibration step is carried out, into a temperature memory unit;
upon receiving a processing start command signal, calculate the difference between said actual temperature and said calibration temperature;
if said difference is higher than a predetermined value, emit an alarm signal,
wherein a means is provided for notifying said alarm signal to a user, so that said user can activate a new calibration cycle of said magnetic field sensors (22).

14. The system (50) according to claim 1, wherein:
said sensor control unit (25) is integral to said support (23);
said data processing unit (30) is an external data processing unit selectively connectable to said sensor control unit (25), in particular said external data processing unit (30) is resident in a personal computer;
and said data collection unit (20) comprises, integral to said support (23)
a non-volatile memory unit (27', 27") for said magnetic field data, and
a housing (60) for an internal battery for electrically supplying said sensor control unit (25) and said magnetic field sensors (22).

15. The system (50) according to claim 1, wherein
said data processing unit (30) is configured to perform a step of calibrating said magnetic field sensors (22);
said data collection unit (20) is arranged to be electrically supplied selectively by an internal battery or by an external power source,
said sensor control unit (25) is configured to discontinue an electric supply of said data collection unit (20) from said internal battery upon receiving an end-of-calibration signal, in particular once a predetermined delay time has elapsed after receiving said end-of-calibration signal.

16. The system (50) according to claim 1, wherein said data processing unit (30) is integral to said support (23).

17. An apparatus (100) for controlling a peripheral device (199) according to the movements of a subject's tongue (la) including the system (50) according to claim 1, wherein said support (23) is configured to be fixedly worn on said subject's head (9) and said magnetic field source (10) is configured to be fixed to said subject's tongue (la), wherein said apparatus (100) comprises an interface and control unit (150) for controlling a peripheral device, said interface and control unit (150) configured to receive said position coordinates of said magnetic field source (10) with respect to said geomagnetic field (5) from said system (50) and to perform a generation of control signals for said peripheral device (199) starting from said position coordinates of said magnetic field source (10).

18. An apparatus according to claim 17, comprising a sound detector connected to said interface and control unit (150), and said interface and control unit (150) comprises a means for recognizing a verbal communication act of said subject and is configured to discontinue said generation of control signals upon recognizing said verbal communication act.

19. An apparatus (200) for controlling a peripheral device (199) according to the movements of a subject's eyeball (1*b*) including the system (50) according to claim 1, wherein said support (23) is configured to be fixedly worn on said subject's head (9) and said magnet is configured to be fixed to of said subject's eyeball (1*b*), wherein said apparatus comprises an interface and control unit (150) for controlling a peripheral device, said interface and control unit (150) configured to receive said position coordinates of said magnetic field source (10) with respect to said geomagnetic field (5) from said system (50), and to perform a generation of control signals for said peripheral device (199) starting from said position coordinates of said magnetic field source (10).

20. An apparatus according to claim 19, wherein said magnetic field source is a magnet (10) configured to be integrally connected to a contact lens (216) wearable by said subject, in particular said magnet (10) has a transversal dimension shorter than 3 mm and a thickness shorter than 1 mm, more in particular, a transversal dimension shorter than 2 mm and a thickness shorter than 0.5 mm.

21. A three-dimensional pointing apparatus (400), in particular a three-dimensional writing device, comprising:
a three-dimensional drawing pad (401) that reproduces a drawing environment or a command environment;
a pointing device (1*c*) comprising a portion (410), in particular a tip portion, that is configured to be displaced in said three-dimensional drawing pad (401);
a display unit (420) configured to perform a representation of graphic elements (421);
a data processing unit (430) configured to order said display unit (420) to perform said representation of said graphic elements (421) responsive to the position and/or to an active/inactive status of said pointing device (1*c*) in said three-dimensional drawing pad (401);
the system (50) according to claim 1, wherein said magnetic field source (10) is arranged at said portion (410) of said pointing device (1*c*), wherein said pointing device (1c) is said object to be tracked (1), and wherein said support (23) is integral to said three-dimensional drawing pad (401).

22. An apparatus according to claim 21, also comprising a shield element of a ferromagnetic material arranged for relatively moving with respect to said magnetic field source (10), in order to shield said magnetic field source (10) at a variable shield degree with respect to said magnetic field sensors (22), so that said system (50), through said magnetic field sensors (22), can detect intensity changes of said local magnetic field (4), and wherein said data processing unit is configured to modify a display parameter of one of said graphic elements (421), in said display unit (420), according to said shield degree, in particular, said display parameter is selected from the group consisting of: a line thickness, a line color, a hatch density.

23. An apparatus (500) for measuring a subject's graphometric features, comprising:
- a pen-like element (1d) configured to be operated by a hand of said subject;
- a sensitive surface (501) configured to feel the contact of a tip (502) of said pen-like element (1d);
- a computing means (520) associated with said sensitive surface (501) configured to associate a plurality of graphometric features to a writing contact of said pen-like element (1d) on said sensitive surface (502),
- the system (50) according to claim 1, wherein said magnetic field source (10) is arranged at a portion (510) of said pen-like element (1d), in particular at an end portion (510) of said pen-like element (1d) opposite to said tip (502) of said pen-like element (1d), wherein said pen-like element (1d) is said object to be tracked (1), and wherein said support (23) is integral to said sensitive surface (501),
- wherein said graphometric features comprise parameters associated with said orientation coordinates of said magnetic field source (10), in particular said graphometric features comprise two inclination angles of said pen-like element (1d) during said writing contact.

24. An apparatus for tracking displacements of a surgical tool in a patient's body, including the system (50) according to claim 1, wherein said magnetic field source (10) is arranged at a portion, in particular at an end portion, of said surgical tool (1e).

25. An apparatus (700) for tracking displacements of the fingers (2) of a subject's hand (3), comprising at least one system (50) according to claim 1, wherein
- said magnetic field source (10) is arranged at a portion (1f) of a respective finger (2) of said hand (3), in particular at a phalanx (1f);
- said support (23) with said array (21) of said magnetic field sensors (22) is configured to be fixed to the wrist (702) of said hand (3) or to the corresponding forearm (703) of said subject.

* * * * *